(12) United States Patent
Nishimori et al.

(10) Patent No.: US 8,950,896 B2
(45) Date of Patent: Feb. 10, 2015

(54) ILLUMINATION APPARATUS

(75) Inventors: Naoki Nishimori, Kyoto (JP); Akira Matsui, Kyoto (JP); Rie Masuda, Kyoto (JP); Jun Ota, Kyoto (JP); Sayuki Nakada, Kyoto (JP); Shingo Inazumi, Kyoto (JP)

(73) Assignee: OMRON Corporation, Kyoto-shi (JP)

( * ) Notice: Subject to any disclaimer, the term of this patent is extended or adjusted under 35 U.S.C. 154(b) by 46 days.

(21) Appl. No.: 13/883,814

(22) PCT Filed: Mar. 16, 2011

(86) PCT No.: PCT/JP2011/056229
§ 371 (c)(1),
(2), (4) Date: May 7, 2013

(87) PCT Pub. No.: WO2012/066797
PCT Pub. Date: May 24, 2012

(65) Prior Publication Data
US 2013/0223071 A1    Aug. 29, 2013

(30) Foreign Application Priority Data

Nov. 15, 2010 (JP) .................................. 2010-254454
Feb. 2, 2011 (JP) .................................. 2011-020895

(51) Int. Cl.
*F21V 5/00* (2006.01)
*F21S 2/00* (2006.01)
(Continued)

(52) U.S. Cl.
CPC ................ *F21V 5/007* (2013.01); *F21S 2/005* (2013.01); *F21V 5/04* (2013.01); *G01N 21/8806* (2013.01); *G01N 21/89* (2013.01); *G01N 21/9036* (2013.01); *F21Y 2101/02* (2013.01)
USPC ........................................................ 362/244

(58) Field of Classification Search
CPC ............ F21V 5/00; F21V 5/007; F21V 5/04; F21V 17/00; F21V 15/00; F21V 15/01; F21S 2/005; F21Y 2101/02; F21Y 2103/02; F21Y 2103/022; G01N 21/8806
See application file for complete search history.

(56) References Cited

U.S. PATENT DOCUMENTS 6,033,087 A * 3/2000 Shozo et al. .................. 362/244
6,070,986 A * 6/2000 Yoneda ........................... 362/33
(Continued)

FOREIGN PATENT DOCUMENTS

CN     201502918 U     6/2010
JP     2006-39330 A    2/2006
(Continued)

OTHER PUBLICATIONS

The office action letter issued on Oct. 28, 2014, in the counterpart Chinese patent application.

*Primary Examiner* — Bao Q Truong
(74) *Attorney, Agent, or Firm* — Marvin A. Motsenbocker; Mots Law, PLLC

(57) ABSTRACT

An illumination apparatus includes lenses, a first casing that has a radiation plane provided with annularly arranged windows for attaching the lenses, respectively, independently, and that has an opening at a position opposite to the radiation plane, and a first substrate associated with each of the lenses and accordingly disposed. The first substrate has at least one light emitting device mounted thereon. The first casing includes a holding portion associated with each of the windows. The holding portion each permits the lens to be attached to the first casing from a side thereof having the opening and also restrains the lens from moving through the first casing toward the radiation plane, and when the lens is attached to the first casing, the lens has an optical axis in a direction having a predetermined angle relative to a center axis of the first casing.

9 Claims, 28 Drawing Sheets

(51) Int. Cl.
*F21V 5/04* (2006.01)
*G01N 21/88* (2006.01)
*G01N 21/89* (2006.01)
*G01N 21/90* (2006.01)
*F21Y 101/02* (2006.01)

(56) References Cited

U.S. PATENT DOCUMENTS

| | | | |
|---|---|---|---|
| 6,120,164 A * | 9/2000 | Libin et al. | 362/269 |
| 6,857,762 B2 * | 2/2005 | Shimokawa et al. | 362/245 |
| 7,226,185 B2 * | 6/2007 | Dolgin et al. | 362/239 |
| 8,491,157 B2 * | 7/2013 | Oba et al. | 362/268 |
| 2006/0139918 A1 * | 6/2006 | Dolgin et al. | 362/232 |
| 2011/0182065 A1 * | 7/2011 | Negley et al. | 362/231 |

FOREIGN PATENT DOCUMENTS

| | | |
|---|---|---|
| JP | 2006-210025 A | 8/2006 |
| JP | 2007-258114 A | 10/2007 |
| JP | 2008-139708 A | 6/2008 |
| JP | 2009-146841 A | 7/2009 |
| JP | 2010-49830 A | 3/2010 |
| WO | 2010/061868 A1 | 6/2010 |

* cited by examiner

FIG.2
(a)
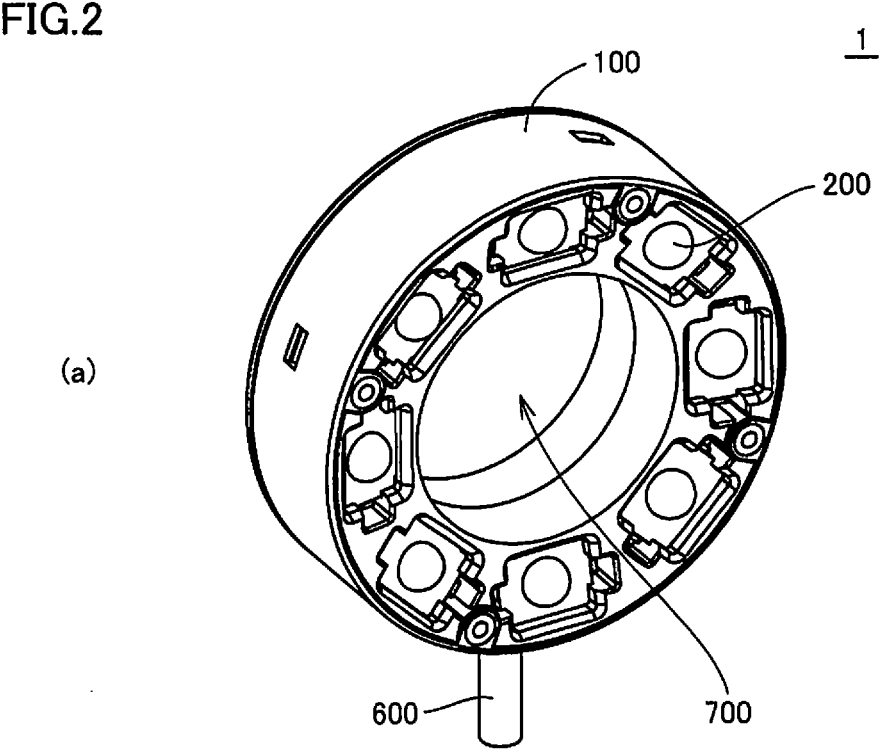
(b)
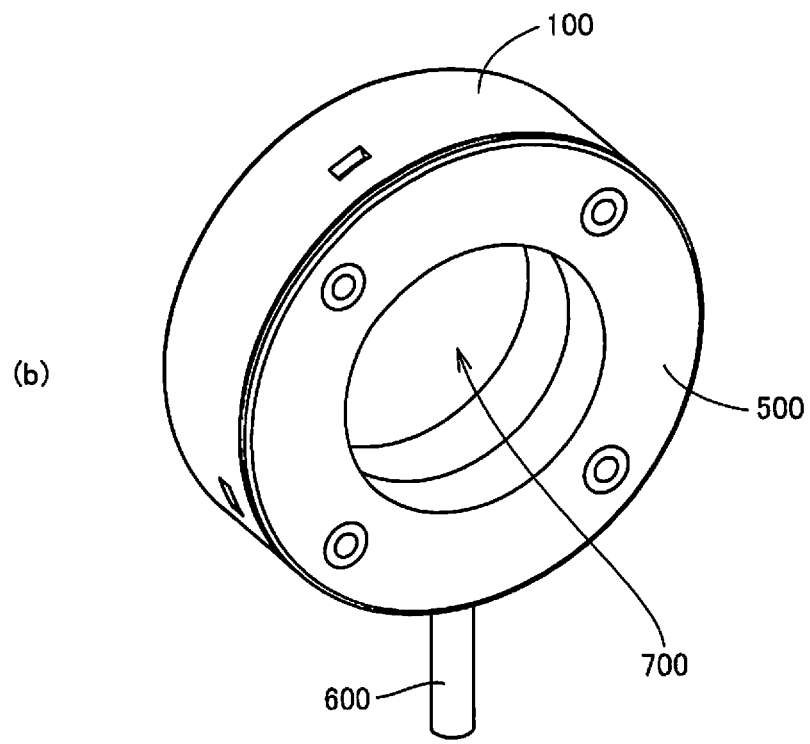

FIG.8
(a)
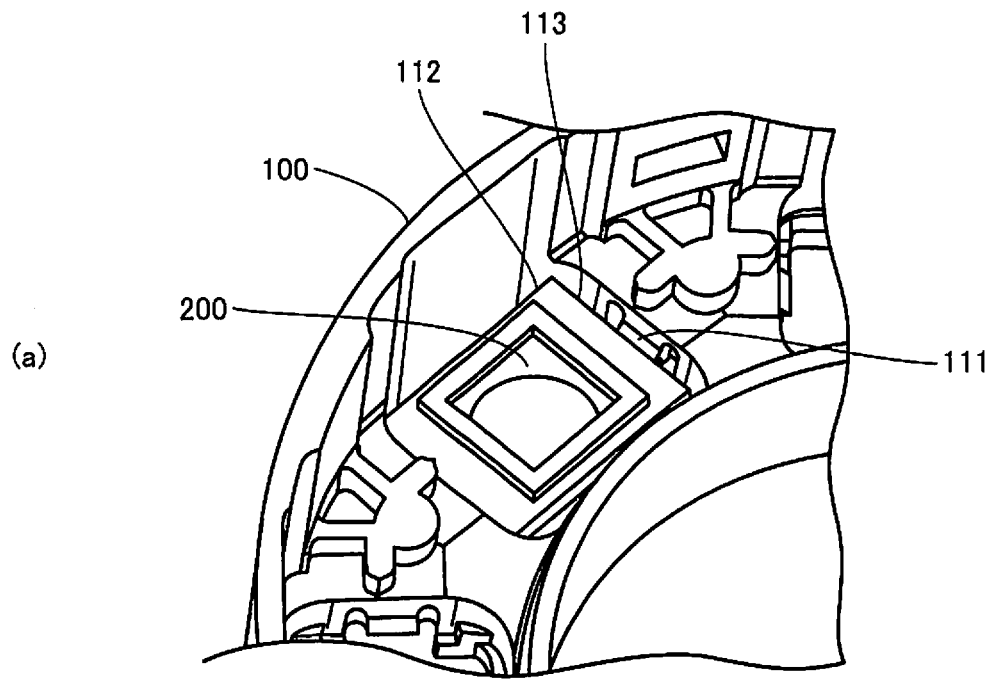
(b)
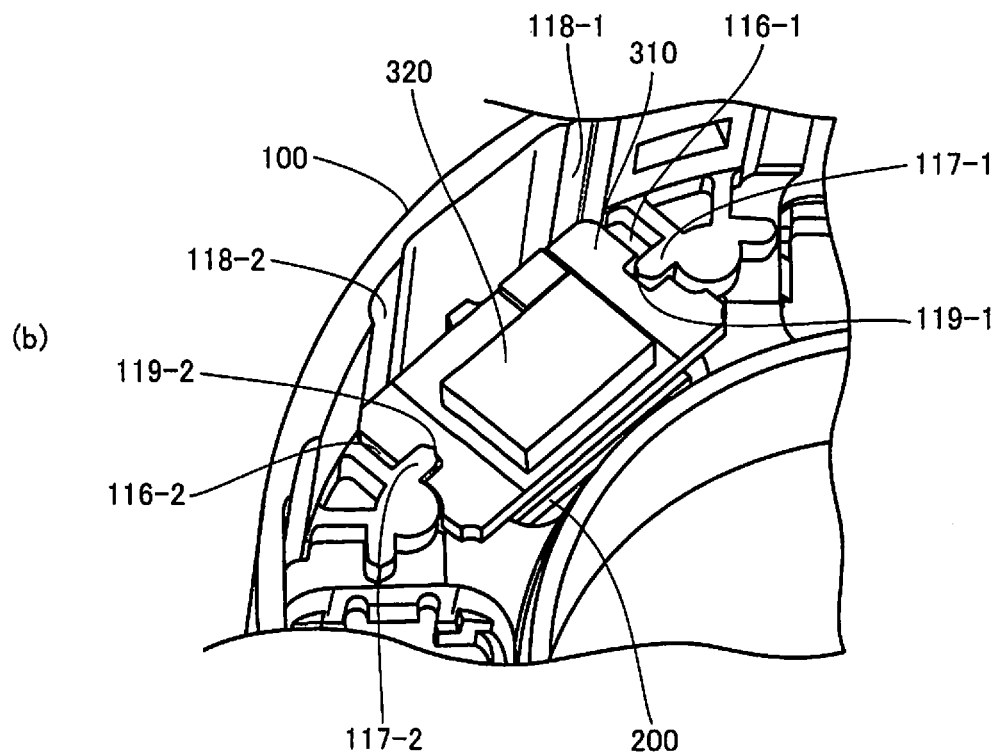

FIG.13
(a) 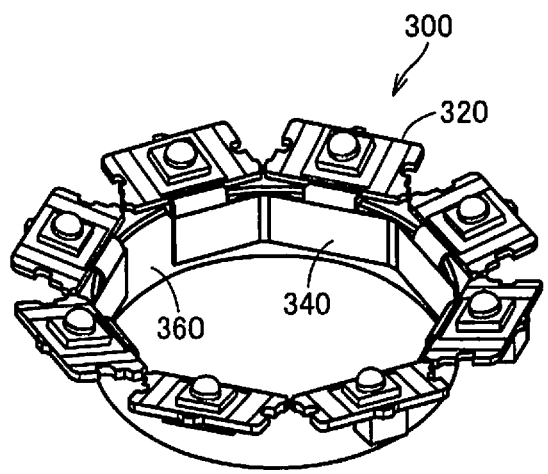
(b) 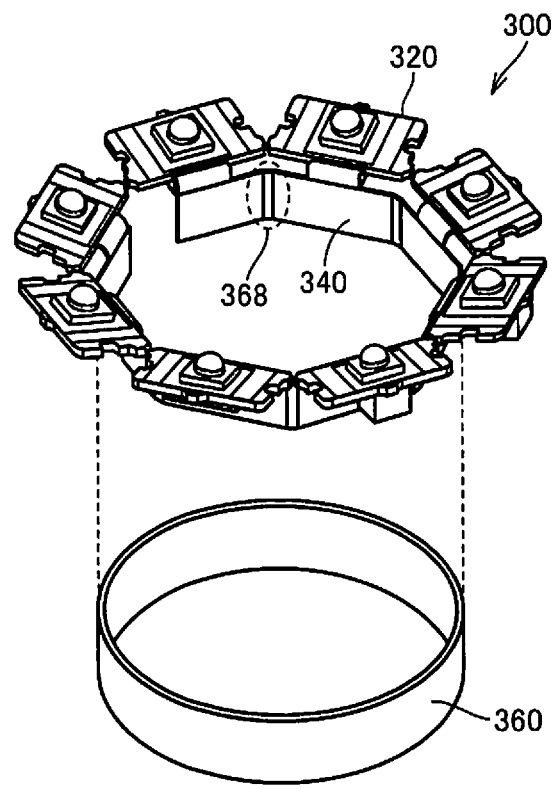

FIG.17
(a)
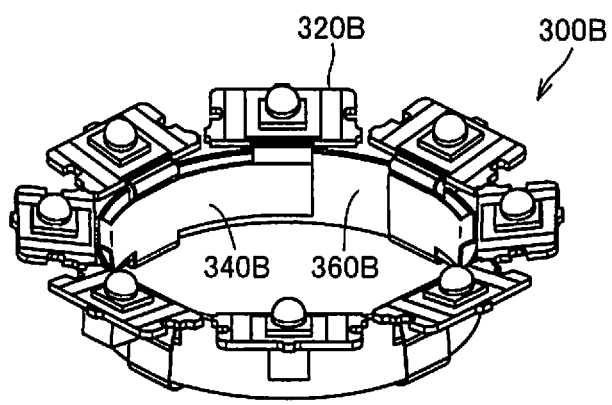
(b)
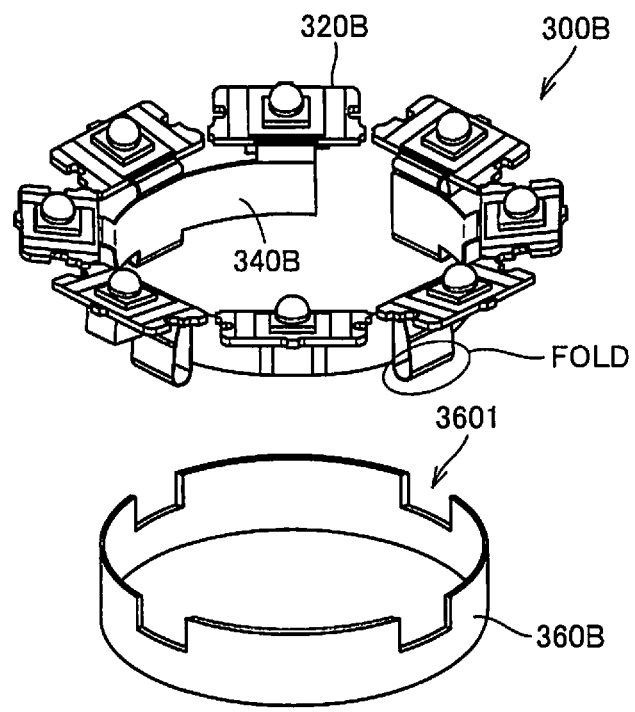

FIG.27
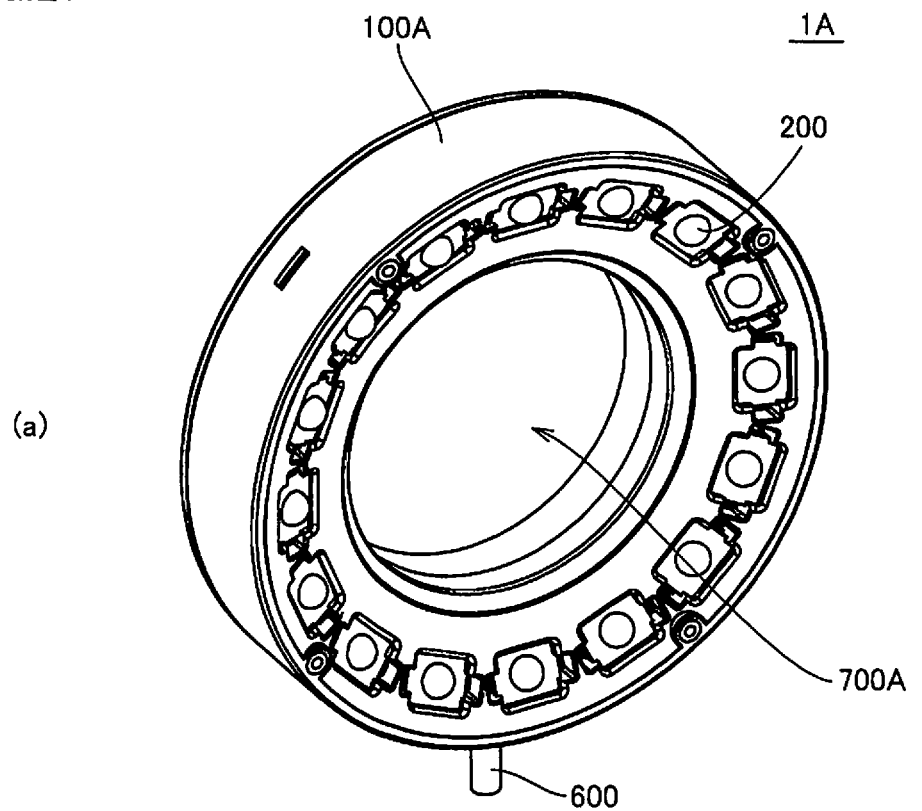
(a)
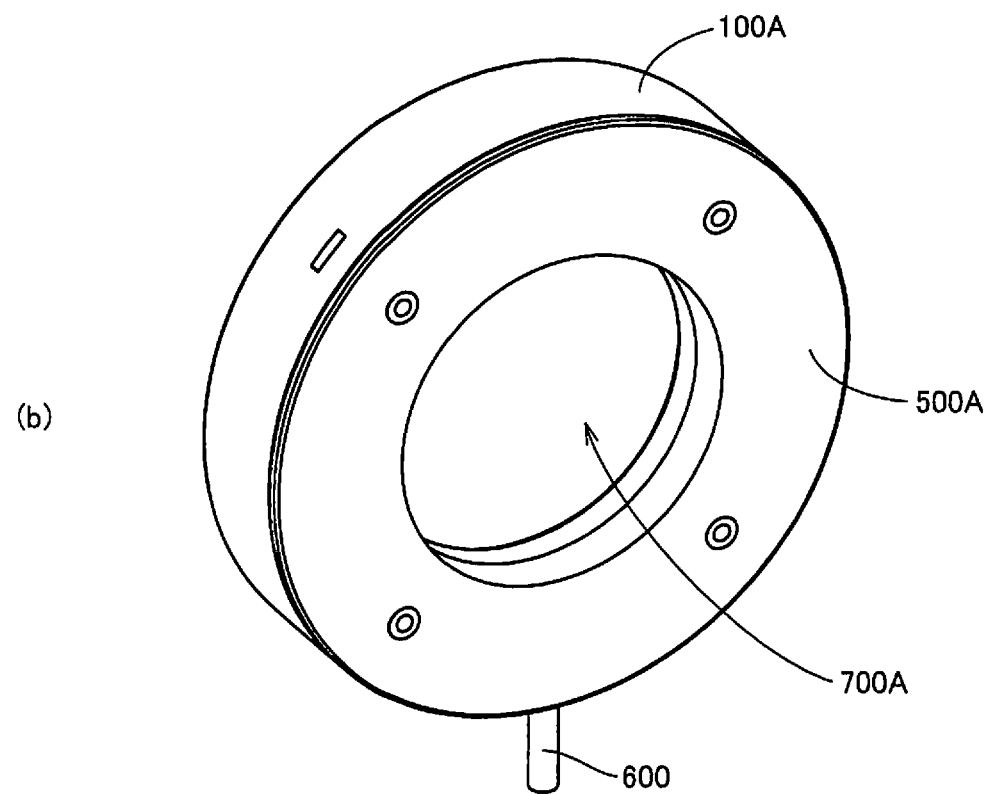
(b)

ILLUMINATION APPARATUS

TECHNICAL FIELD

The present invention relates to an illumination apparatus having a light emitting device, and more particularly to a ring-shaped illumination apparatus for illuminating an object to be imaged when an image is captured.

BACKGROUND ART

In the field of FA (Factory Automation), a variety of image processing techniques are used. Typically, an image processing technique of recognizing characters printed on a test object or inspecting a test object for defects and the like on its surface based on image data obtained by capturing an image of the test object is widely used in practice.

When a variety of measurement processing is performed on a test object using such an image processing technique, it is necessary to acquire an image representing the test object appropriately. Therefore, an illumination apparatus for illuminating a test object is often provided to ensure an appropriate illuminance during image capture. Illumination apparatuses using long-life and low-power-consumption LEDs (Light Emitting Diode) are in practical use.

For example, a ring-shaped illumination apparatus disclosed in Japanese Patent Laying-Open No. 2008-139708 (PTL 1) is configured to include a plurality of concentrically arranged LED rows and a plurality of optical members concentrically arranged to correspond to the LED rows. The manner in which the LED row illuminate a work is different from one another. The optical members are continuous to form an integral structure. Accordingly, a single apparatus can be adapted for different kinds of object lens and work.

An LED illumination apparatus disclosed in Japanese Patent Laying-Open No. 2009-146841 (PTL 2) is structured such that a positioning pin provided on a flat base is inserted into a through hole provided on a flat LED substrate having a plurality of LEDs thereon and into a positioning pin insertion hole provided on an integral lens holder for holding a plurality of lenses, whereby the lens holder is positioned with respect to the LED substrate. Accordingly, individual lenses can be positioned with respect to a plurality of LEDs.

CITATION LIST

Patent Literature

PTL 1: Japanese Patent Laying-Open No. 2008-139708
PTL 2: Japanese Patent Laying-Open No. 2009-146841

SUMMARY OF INVENTION

Technical Problem

The image processing technique in the field of FA as described above is requested to be able to measure a wide variety of test objects. Test objects range, for example, from small electronic components to finished products such as automobiles. Therefore, it is preferable that illumination apparatuses should be offered with a lineup of many variations (products) as to illumination view and illumination distance (work distance) in order to adapt to a wide variety of applications.

In order to have a lineup of many variations (products), it is preferable that a light emitting device should be combined with a lens for optical path control.

As the shape of the illumination apparatus, a ring shape is often adopted in which light emitting devices are concentrically disposed around a center hole. The adoption of the ring shape allows a work to be radiated uniformly with light and enables more appropriate image capture.

On the other hand, in such a ring-shaped illumination apparatus, each light emitting device, which applies light toward a work positioned on the axis of the center hole, is attached to have the optical axis at an angle with respect to the axis of the center hole.

In the ring-shaped illumination apparatus disclosed in PTL 1, as many kinds of lenses as variations in field of view and work distance have to be prepared, which may lead to cost increase. In the LED illumination apparatus disclosed in PTL 2, there is a limit to variations allowed for the field of view and the work distance since the light emitting devices and lenses cannot be inclined. In addition, there is a possibility that the lens drops toward a work since the lens is arranged in the lens holder on the side having the light radiation plane. Therefore, the illumination apparatus is not suitable for a vision sensor for FA.

The present invention is therefore made to solve these problems. An object of the present invention is to provide a ring-shaped illumination apparatus which can be offered with a lineup of different kinds with different specifications while preventing cost increase and reliability reduction.

Solution to Problem

An illumination apparatus in the present invention includes a plurality of lenses, a first casing that has a radiation plane provided with a plurality of annularly arranged windows for attaching the plurality of lenses, respectively, independently, and that has an opening at a position opposite to the radiation plane, a first substrate associated with each of the plurality of lenses and accordingly disposed, and a second casing closing the opening of the first casing. The first substrate each has at least one light emitting device mounted thereon. The first casing includes a holding portion associated with each of the plurality of windows. The holding portion each permits the lens to be attached to the first casing from a side thereof having the opening and also restrains the lens from moving through the first casing toward the radiation plane, and when the lens is attached to the first casing the lens has an optical axis in a direction having a predetermined angle relative to a center axis of the first casing.

Preferably, the illumination apparatus further includes a second substrate for electrical connection between the first substrate and another first substrate. The first substrate is configured as a rigid body. The second substrate is configured to have flexibility.

Further preferably, the second substrate is bent in accordance with how the plurality of windows are arranged. The first substrate is each bent relative to an associated portion of the second substrate at an angle corresponding to an inclination of the lens held by the holding portion.

Further preferably, the holding portion each further holds the first substrate to maintain a predetermined, relative, positional relationship with the lens.

Preferably, the second casing includes a pressing portion for pressing each first substrate that has been attached to the first casing toward the radiation plane when the second casing is coupled with the first casing.

Further preferably, the pressing portion is each configured to press opposite ends of the first substrate associated therewith.

Further preferably, the illumination apparatus further includes a heat conducting and elastic sheet inserted between the first substrate and the pressing portion of the second casing.

Further preferably, the sheet is generally round, and also has a cut and is thus sectioned to correspond to how the first substrate is arranged.

Preferably, the illumination apparatus further includes a power supply cable penetrating the first and second casings and thus introduced therein. The second substrate includes a pair of connectors for electrical connection to the power supply cable. The pair of connectors are provided in a direction corresponding to a position at which the power supply cable is introduced.

Advantageous Effects Of Invention

The present invention provides a ring-shaped illumination apparatus which can be offered with a lineup of different kinds with different specifications while preventing cost increase and reliability reduction.

BRIEF DESCRIPTION OF DRAWINGS

FIG. 2 is a perspective view showing an appearance of the illumination apparatus according to the embodiment of the present invention.

FIG. 8 is a diagram illustrating a structure of the holding portion formed at the base of the illumination apparatus according to the embodiment of the present invention.

FIG. 13 is a diagram illustrating an auxiliary fixing member attached to the rigid flexible substrate of the illumination apparatus according to the embodiment of the present invention.

FIG. 17 is a diagram illustrating an auxiliary fixing member attached to the modification of the rigid flexible substrate of the illumination apparatus according to the embodiment of the present invention.

FIG. 27 is a perspective view showing an appearance of the illumination apparatus according to a modification of the embodiment of the present invention.

DESCRIPTION OF EMBODIMENTS

Figure 1:
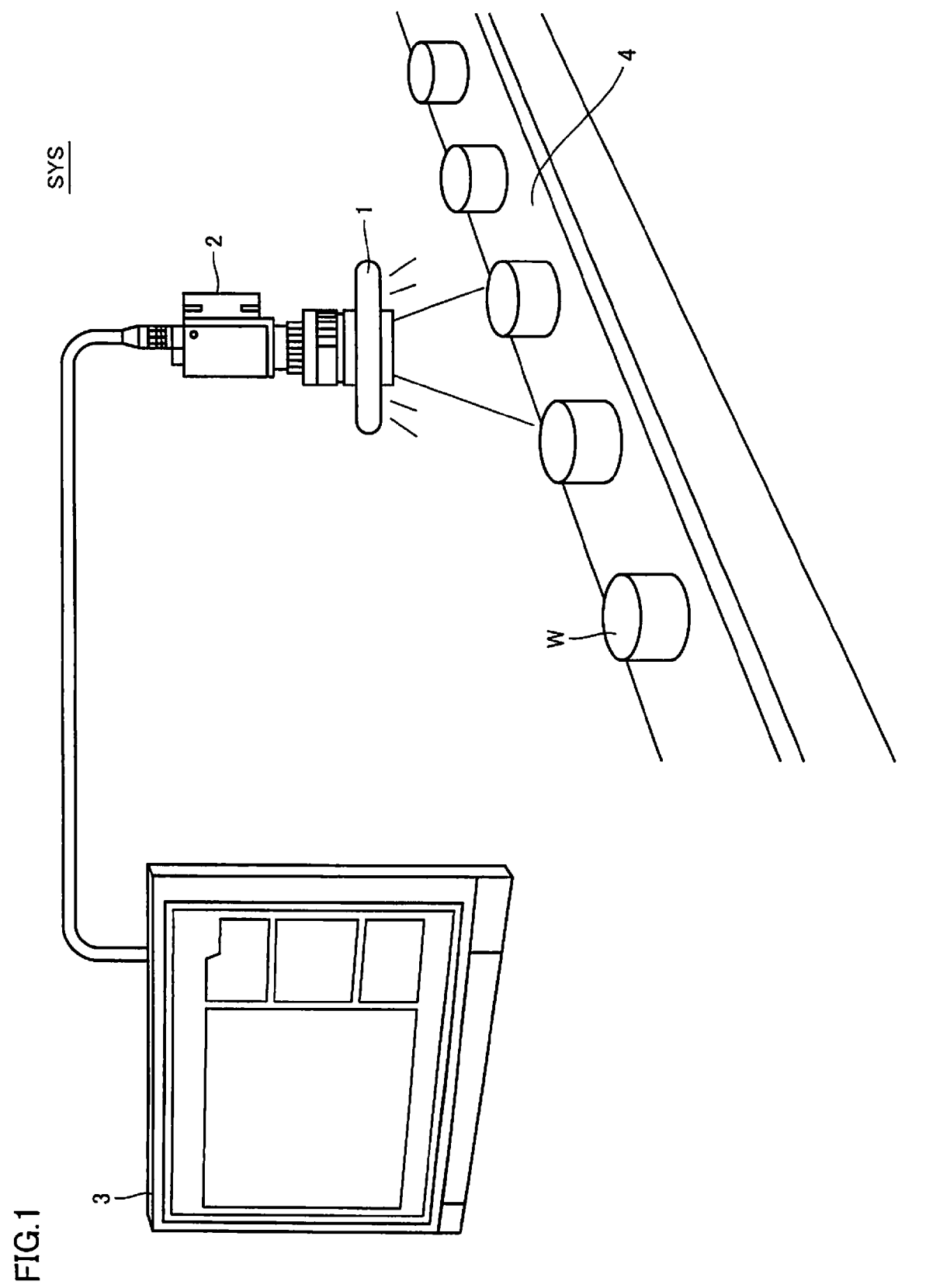
FIG. 1 is a schematic diagram showing an overview of a vision sensor system using an illumination apparatus according to an embodiment of the present invention.

Embodiments of the present invention will be described in detail with reference to the figures. It is noted that the same or corresponding parts in the figures are denoted with the same reference numerals and a description thereof will not be repeated.

<<A. System Configuration>>

FIG. 1 is a schematic diagram showing an overview of a vision sensor system SYS using an illumination apparatus according to an embodiment of the present invention. Referring to FIG. 1, the vision sensor system SYS is typically installed in a production line to perform processing (measurement processing) such as character recognition and defect inspection based on images obtained by capturing an image of a test object (work).

More specifically, the vision sensor system SYS includes an image processing apparatus 3, a camera 2 connected to image processing apparatus 3, and a ring-shaped (doughnut-shaped) illumination apparatus 1 for illuminating the field of view of camera 2 and the proximity thereof. Camera 2 captures an image of a work W conveyed on a production line 4 at an appropriate timing to generate image data and outputs the generated image data to image processing apparatus 3.

Image processing apparatus 3 is a computer including a CPU (Central Processing Unit), a memory, and the like and, in the example shown in FIG. 1, is configured integrally with a display for displaying a measurement processing result and the like.

Illumination apparatus 1 in the present embodiment uses a light emitting device such as an LED (Light Emitting Diode) as a light source. A bullet-type LED, a surface mount-type LED, a bare chip mount-type LED, and the like may be adopted as the light source of illumination apparatus 1 according to variations in shape and mounting manner. In particular, the illumination apparatus in the present embodiment is suitable when a surface mount-type chip LED or a bare chip mount-type LED is adopted.

Although FIG. 1 shows a configuration in which illumination apparatus 1 is attached in the periphery of camera 2, illumination apparatus 1 may be disposed in proximity to or at a distance from work W with respect to camera 2.

<<B. Appearance of Illumination Apparatus>>

Referring now to FIG. 2, the appearance of illumination apparatus 1 in the present embodiment will be described.

FIG. 2 is a perspective view showing an appearance of illumination apparatus 1 according to the embodiment of the present invention. Here, FIG. 2(a) represents the side having a radiation plane of illumination apparatus 1, and FIG. 2(b) represents the back side of illumination apparatus 1.

As shown in FIG. 2(a) and FIG. 2(b), illumination apparatus 1 is generally ring-shaped. More specifically, illumination apparatus 1 includes a base 100 corresponding to a first casing and a case 500 corresponding to a second casing. As described later, base 100 and case 500 are fitted together, for example, by means of snap fits to form an integral ring shape.

A plurality of concentrically disposed lenses 200 are attached to be exposed on the radiation plane of base 100. The radiation plane of base 100 is formed as an inclined plane to have a prescribed angle relative to the center axis of a center hole 700 formed to pass through base 100 and case 500.

A unit substrate having a light emitting device mounted thereon is associated with each lens 200 and accordingly disposed in case 500. A power supply cable 600 for supplying power to the light emitting devices is attached through a notch formed on a side surface of case 500.

<<C. Basic Structure>>

Figure 3:
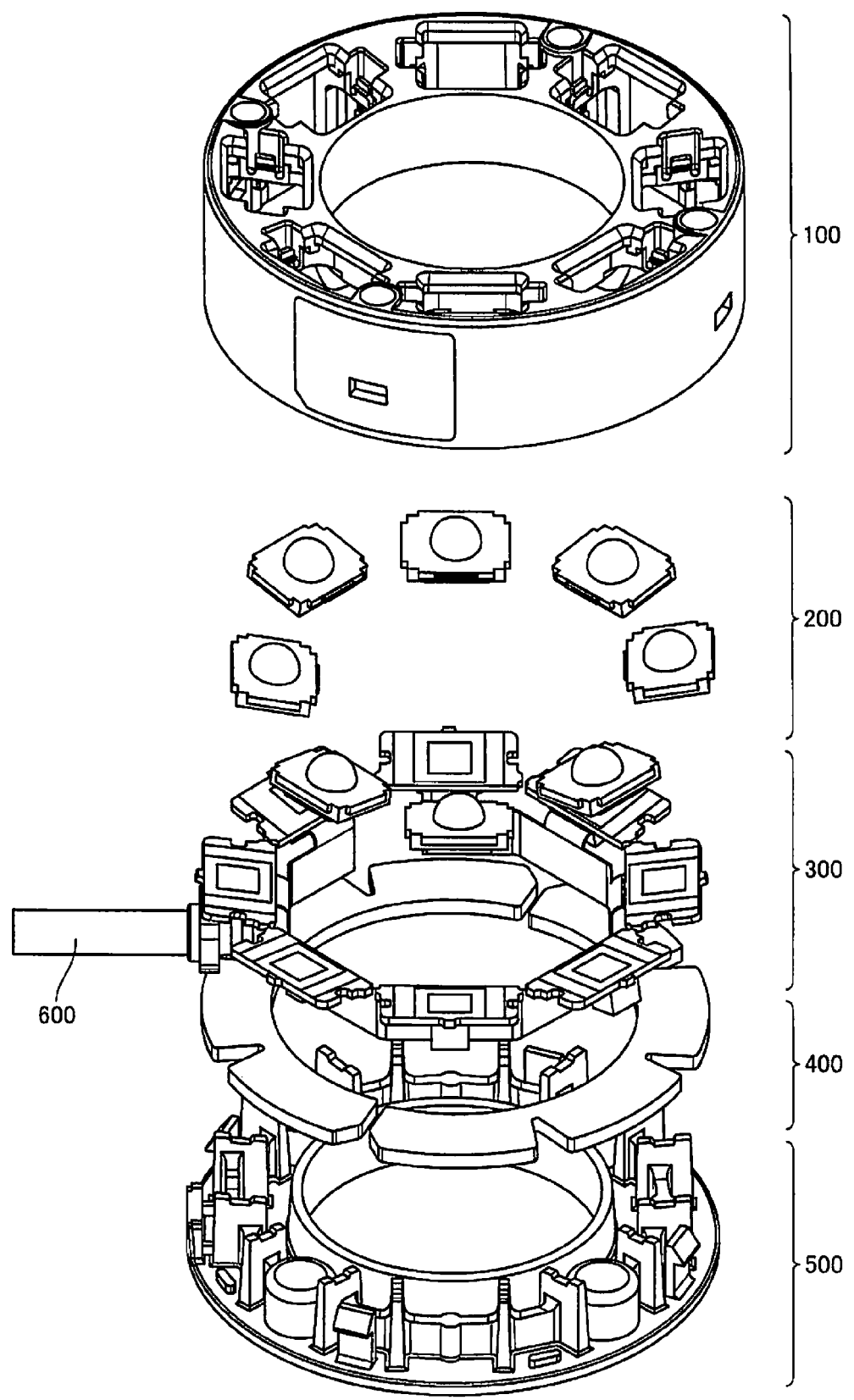
FIG. 3 is an exploded perspective view of the illumination apparatus according to the embodiment of the present invention.
Figure 4:
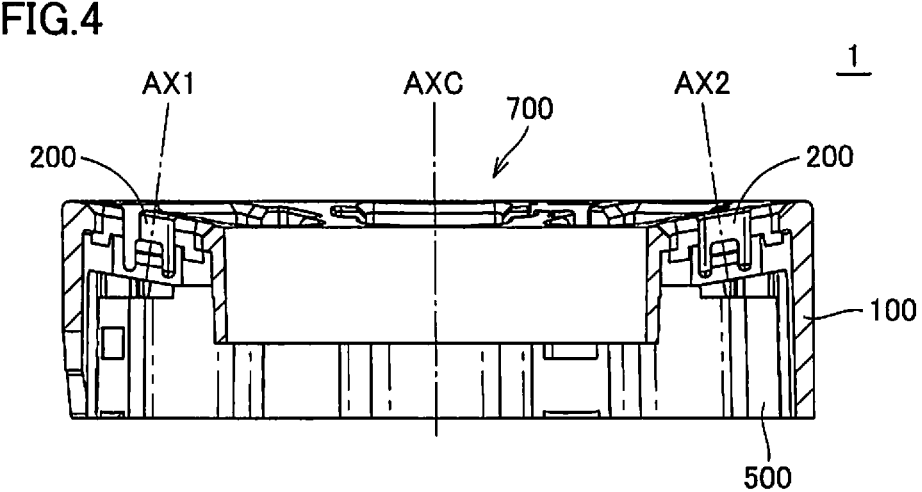
FIG. 4 is a cross-sectional view of the illumination apparatus according to the embodiment of the present invention.

Referring now to FIG. 3 and FIG. 4, a basic configuration of illumination apparatus 1 will be described.

FIG. 3 is an exploded perspective view of illumination apparatus 1 according to the embodiment of the present invention. FIG. 4 is a cross-sectional view of illumination apparatus 1 according to the embodiment of the present invention.

Referring to FIG. 3, in illumination apparatus 1, lens 200 is attached to ring-shaped base 100 from the back side. As described later, a window of base 100 to which lens 200 is attached is provided with a holding portion for holding lens 200 and for restraining lens 200 from moving through base 100 toward the radiation plane (exposed surface).

A rigid flexible substrate 300 formed in a concentric shape is disposed to correspond to the form in which lenses 200 are disposed. Rigid flexible substrate 300 includes unit substrates on which light emitting devices associated with a plurality of concentrically disposed lenses 200 are mounted. Rigid flexible substrate 300 is supplied with power for driving the light emitting devices through power supply cable 600.

A generally round heat sink sheet 400 for dissipating heat generated by the light emitting devices on rigid flexible substrate 300 is inserted between rigid flexible substrate 300 and case 500. Heat sink sheet 400 is formed of an elastic material and also functions as a cushion material or a pressing portion for lenses 200 and rigid flexible substrate 300 inserted into a space between base 100 and case 500.

Case 500 has a convex portion on a surface thereof facing base 100 for fixing each set of lens 200 and the unit substrate having a light emitting device mounted thereon.

As shown in FIG. 4, each lens 200 is positioned such that its optical axis is generally perpendicular to the radiation plane of base 100 at the position at which it is disposed. Therefore, the optical axis of each lens 200 is not parallel to the center axis of center hole 700 but is held at a prescribed angle corresponding to the inclination angle of the radiation plane. Specifically, the optical axis (optical axes AX1 and AX2) of each lens 200 is non-parallel to the center axis (optical axis AXC) of center hole 700. The optical axes (optical axes AX1 and AX2) of lenses 200 are also non-parallel to each other.

<<D. Assembly Procedure>>

Figure 5:
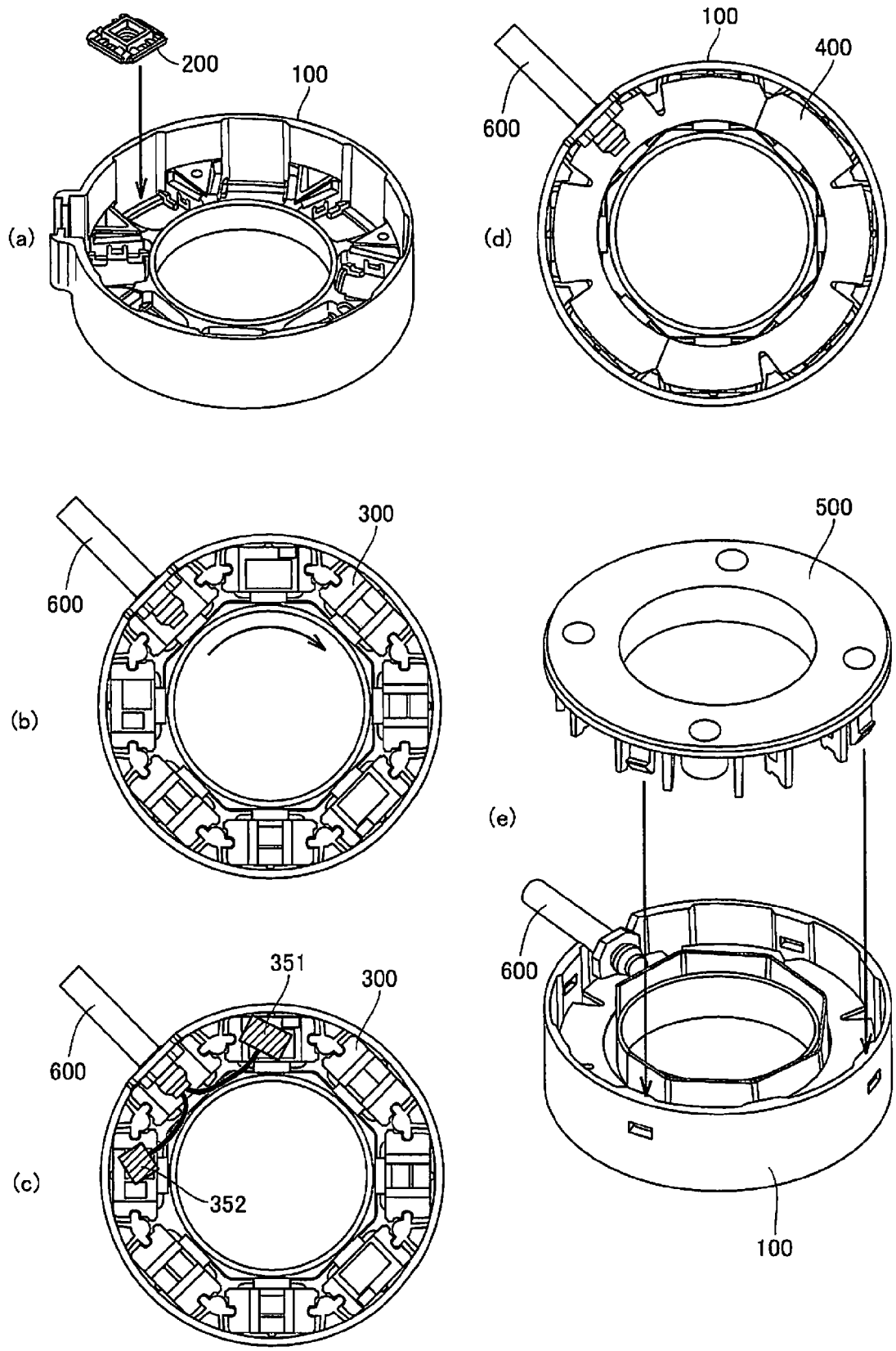
FIG. 5 is a schematic diagram showing an assembly procedure of the illumination apparatus according to the embodiment of the present invention.

Referring now to FIG. 5, an assembly procedure of illumination apparatus 1 will be described.

FIG. 5 is a schematic diagram showing an assembly procedure of illumination apparatus 1 according to the embodiment of the present invention. Here, FIG. 5(a) shows a step of attaching lenses 200 to base 100, FIG. 5(b) shows a step of attaching rigid flexible substrate 300 associated with lenses 200, FIG. 5(c) shows a step of attaching the power supply cable to rigid flexible substrate 300, FIG. 5(d) shows a step of attaching heat sink sheet 400, and FIG. 5(e) shows a step of fitting base 100 and case 500 together.

As shown in FIG. 5(a), as a first step, lenses 200 are attached to the respective windows from the back side (the opening side) of base 100. Here, the holding portion for holding lens 200 is formed at each window. Lens 200 is fixed to base 100 by fitting lens 200 into the holding portion.

Next, as shown in FIG. 5(b), rigid flexible substrate 300 is attached such that the unit substrates are associated with the respective lenses 200. Rigid flexible substrate 300 includes a plurality of unit substrates each having a chip LED mounted on the surface thereof. The member formed at the window of base 100 is configured to hold lens 200 as well as each unit substrate of rigid flexible substrate 300. This structure ensures optical coupling between lens 200 and the light emitting device (unit substrate).

Next, as shown in FIG. 5(c), power supply cable 600 is connected to a pair of connectors 351 and 352 formed on rigid flexible substrate 300. A wiring pattern is formed on rigid flexible substrate 300 such that a plurality of light emitting devices are connected in series. A positive electrode supplied through power supply cable 600 is connected to one end of the series connection, and a negative electrode is connected to the other end of the series connection.

Then, as shown in FIG. 5(d), heat sink sheet 400 is disposed on the top of rigid flexible substrate 300. Finally, as shown in FIG. 5(e), case 500 is attached to base 100, whereby illumination apparatus 1 is completed. Base 100 and case 500 may be integrated using an adhesive or the like. Preferably, they are fitted together using snap fits or the like in order to save time and effort of fabrication.

The details of each component will be described below.

<<E. Details of Base>>

Figure 6:
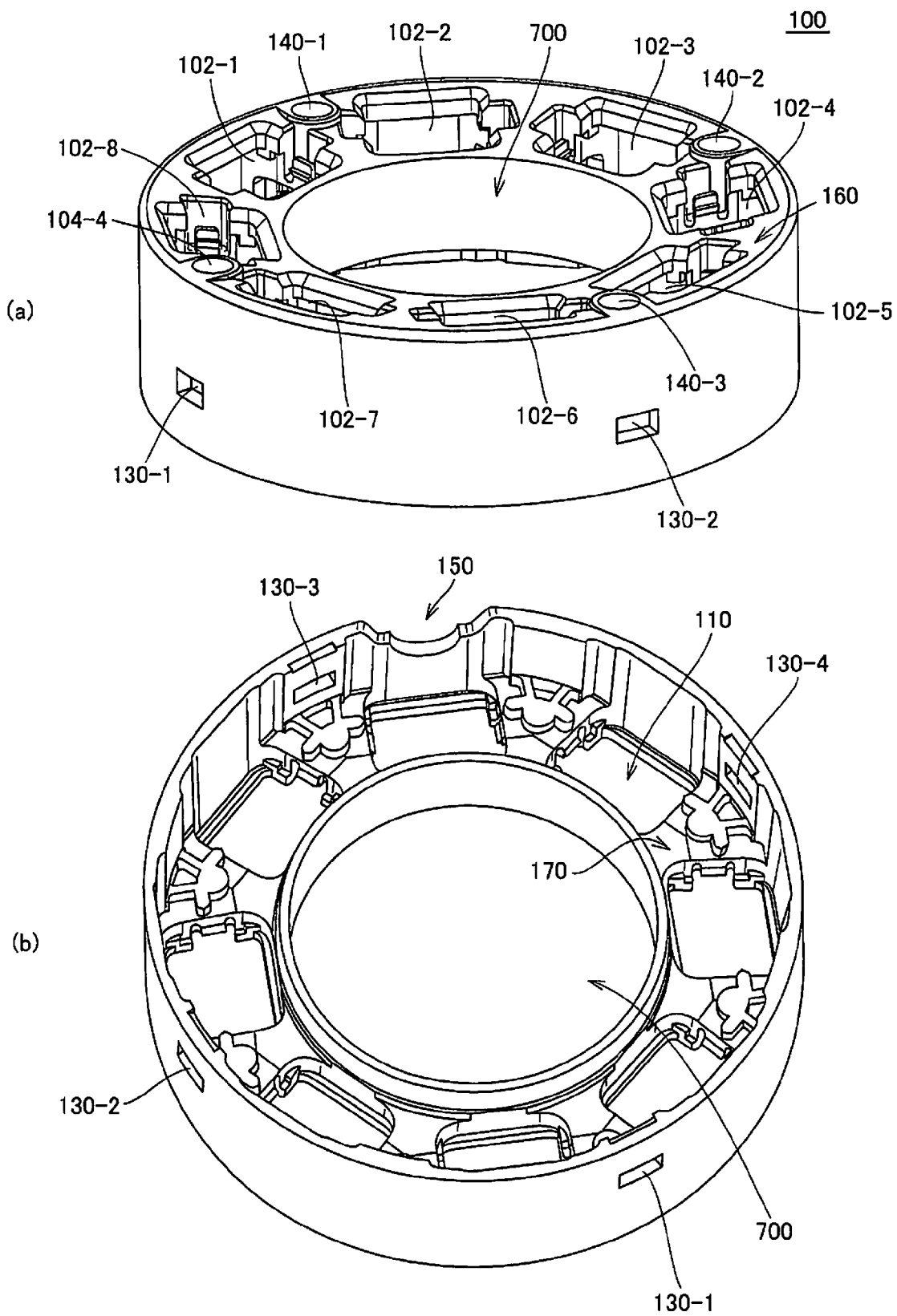
FIG. 6 is a perspective view showing an appearance of a base of the illumination apparatus according to the embodiment of the present invention.
Figure 7:
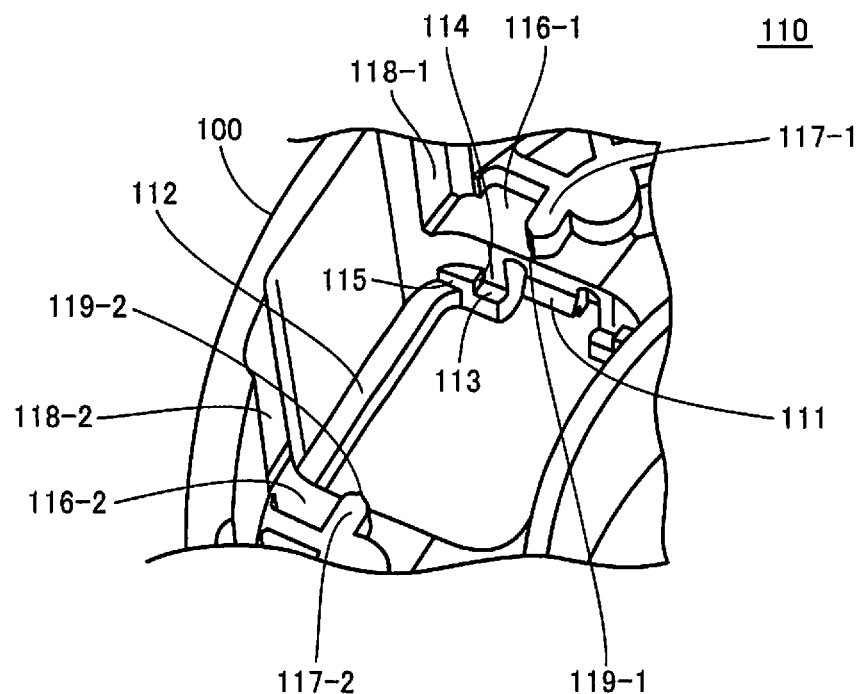
FIG. 7 is a diagram illustrating a structure of a holding portion formed at the base of the illumination apparatus according to the embodiment of the present invention.

Referring now to FIG. 6 to FIG. 8, base 100 of illumination apparatus 1 in the present embodiment will be described.

FIG. 6 is a perspective view showing an appearance of base 100 of illumination apparatus 1 according to the embodiment of the present invention. Here, FIG. 6(a) represents the side having a radiation plane 160 of base 100, and FIG. 6(b) represents the back side (the opening side) of base 100. FIG. 7 and FIG. 8 illustrate a structure of the holding portion formed at base 100 of illumination apparatus 1 according to the embodiment of the present invention.

As shown in FIG. 6(a), windows 102-1 to 102-8 for attaching lenses 200 are formed on radiation plane 160 of base 100 along the inclined surface thereof. Windows 102-1 to 102-8 are disposed concentrically with respect to the center axis of center hole 700. In other words, base 100 that is the first casing has radiation plane 160 provided with annually arranged windows 102-1 to 102-8 for attaching a plurality of lenses 200, respectively, independently and has an opening 170 at a position opposite to radiation plane 160.

Screw holes 140-1 to 140-4 are provided on the radiation plane of base 100 to allow a not-shown diffusion plate to be affixed.

Fitting holes 130-1 to 130-4 are provided on an outer circumferential surface of base 100 for engagement with case 500. Fitting holes 130-1 to 130-4 are engaged with the snap fits provided on case 500, whereby case 500 is fixed to base 100. In other words, case 500 that is the second casing is configured to close the opening of base 100 that is the first casing.

As shown in FIG. 6(b), the outer circumferential surface of base 100 is partially notched to provide a power supply cable-through concave portion 150 to introduce power supply cable 600 to the inside of base 100.

Holding portion 110 associated with each of windows 102-1 to 102-8 as shown in FIG. 6(b) will now be described with reference to FIG. 7 and FIG. 8.

Referring to FIG. 7, holding portion 110 associated with each of windows 102-1 to 102-8 has a configuration for holding lens 200 and each unit substrate 320 (FIG. 8) of rigid flexible substrate 300 (FIG. 8).

Holding portion 110 permits lens 200 to be attached to base 100 that is the first casing from the side thereof having the opening and also restrains lens 200 from moving through base 100 toward the side having the radiation plane. Furthermore, holding portion 110 is configured such that when lens 200 is attached lens 200 has an optical axis (the optical axes AX 1 and AX2 shown in FIG. 4) in a direction having a predetermined angle relative to the center axis (the optical axis AXC shown in FIG. 4) of base 100. As shown in FIG. 4, the optical axes AX1 and AX2 of lens 200 are non-parallel to the optical axis AXC of center hole 700.

More specifically, members for positioning lens 200 include a snap fit 111, bottom holding portions 112 and 113, side restraining portions 114 and 115, bottom holding portions 116-1 and 116-2, light press-fitting pawls 117-1 and 117-2, and side restraining portions 118-1 and 118-2.

More specifically, referring to FIG. 7 and FIG. 8(a), snap fit 111 engages with lens 200 to position lens 200 in the direction of the optical axis and to restrain lens 200 from moving. Lens 200 engaged with snap fit 111 is held at the bottom surface thereof by bottom holding portions 112 and 113. Accordingly, lens 200 is restrained from moving through base 100 toward the exposed surface. Lens 200 engaged with snap fit 111 is also restrained at the side surface thereof by side restraining portions 114 and 115 and is thus positioned in the direction orthogonal to the direction of the optical axis of lens 200.

Referring to FIG. 7 and FIG. 8(b), light press-fitting pawl 117 engages with each unit substrate 320 of rigid flexible substrate 300 to position unit substrate 320 in the direction of the optical axis and to restrain unit substrate 320 from moving. Unit substrate 320 engaged with light press-fitting pawl 117 is held at the bottom surface thereof by bottom holding portions 116-1 and 116-2. Accordingly, unit substrate 320 is restrained from moving through base 100 toward the exposed surface. Unit substrate 320 is also restrained at the side surface thereof by side restraining portions 118-1 and 118-2 and is thus positioned in the direction orthogonal to the direction of the optical axis of lens 200.

In short, holding portion 110 holds unit substrate 320 that is the first substrate to maintain a predetermined relative positional relationship with lens 200.

In illumination apparatus 1 in the present embodiment, a prescribed space for cooling is formed between lens 200 and unit substrate 320.

In this manner, lens 200 and each unit substrate 320 of rigid flexible substrate 300 are assembled with reference to base 100, so that the positional accuracy of lens 200 and the light emitting device can be maintained at the same degree as the accuracy of molding base 100. In other words, as the position of lens 200 and the angle of affixing lens 200 to base 100 are determined by holding portion 110 provided at base 100, molding the base 100 at an appropriate accuracy ensures the desired accuracy of illumination apparatus 1 as a whole.

With provision of such holding portion 110, lens 200 is attached to base 100 from the back side (the opening side) and is restrained from moving toward the radiation plane. Illumination apparatus 1 is often installed such that the radiation plane thereof faces downward in the direction of gravity. Even in such a use environment, dropping of lens 200 toward the work can be avoided.

Lenses 200 and unit substrates 320 can be held by attaching lenses 200 to windows 102-1 to 102-8 of base 100 and thereafter lightly press-fitting unit substrates 320 of rigid flexible substrate 300, thereby simplifying the subsequent assembly operation including connection of power supply cable 600 and engagement of case 500 with base 100.

<<F. Details of Lens>>

Figure 9:
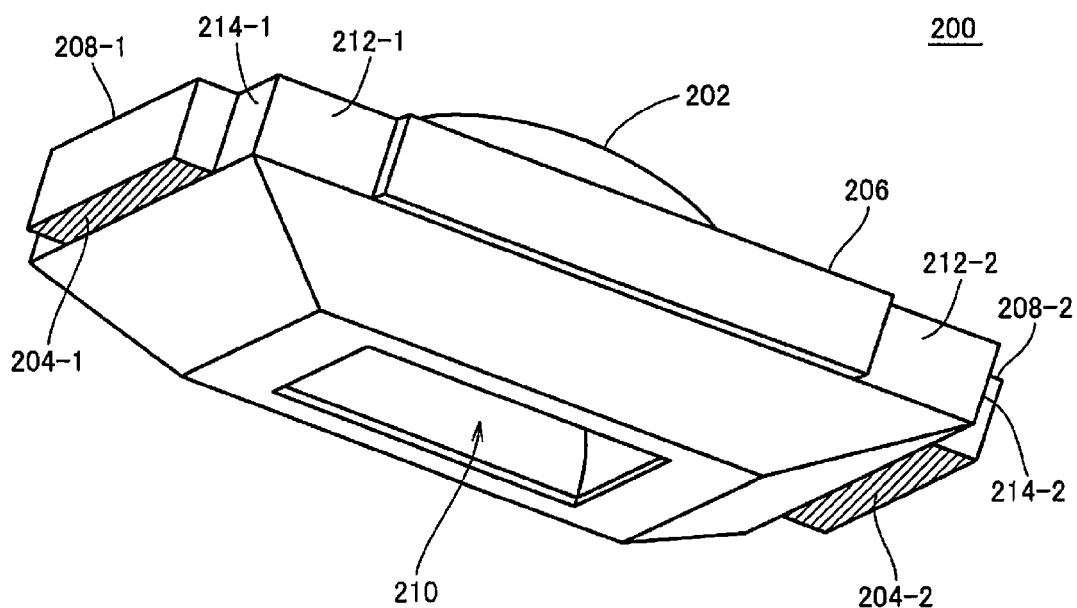
FIG. 9 is a perspective view showing an appearance of a lens of the illumination apparatus according to the embodiment of the present invention.
Figure 10:
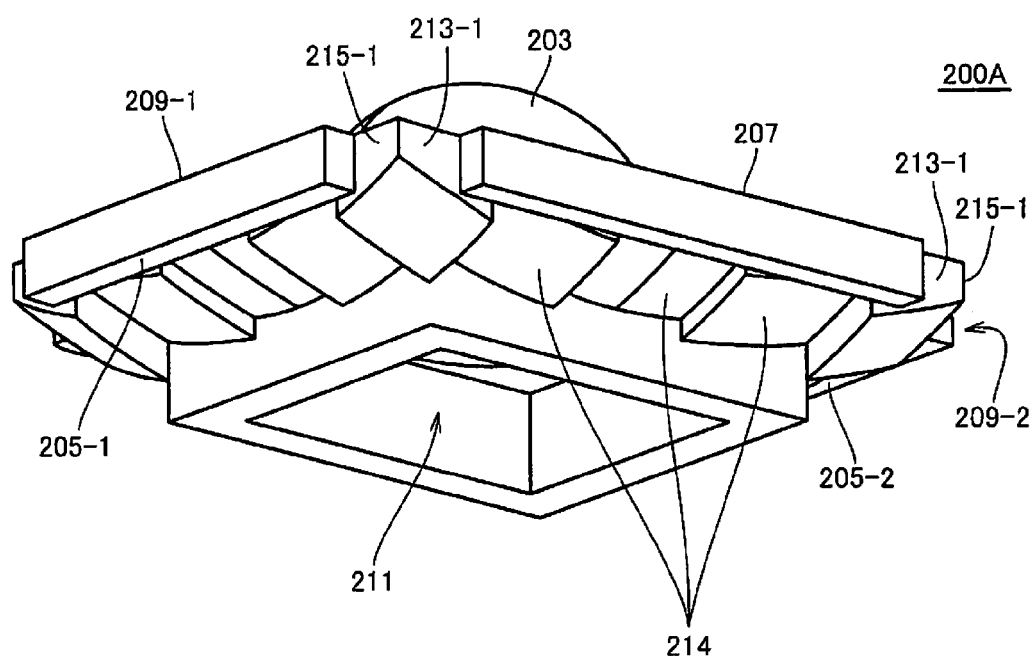
FIG. 10 is a perspective view showing an appearance of a lens in a different manner of the illumination apparatus according to the embodiment of the present invention.

Referring now to FIG. 9 and FIG. 10, lens 200 of illumination apparatus 1 in the present embodiment will be described.

FIG. 9 is a perspective view showing an appearance of lens 200 of illumination apparatus 1 according to the embodiment of the present invention. FIG. 10 is a perspective view showing an appearance of lens 200A in a different manner of illumination apparatus 1 according to the embodiment of the present invention.

Referring to FIG. 9, lens 200 has a concave portion 210 at the center portion thereof in which a light emitting device mounted on unit substrate 320 of rigid flexible substrate 300 is accommodated. Concave portion 210 is in communication with a convex portion 202 on the upper side in the figure. Light generated by the light emitting device radiates in a prescribed direction through convex portion 202. Convex portion 202 is formed integrally with a generally quadrangular base portion. The base portion is provided with lugs associated with the sides.

Among these, a pair of lugs corresponds to contact surfaces 204-1 and 204-2 engaged with snap fits 111 shown in FIG. 7 and FIG. 8. In other words, contact surfaces 204-1 and 204-2 engage with snap fits 111, respectively. In addition, the lugs have contact surfaces 208-1, 208-2, and 206 engaged with bottom holding portions 112 and 113 of holding portion 110.

Provided at four corners of the base portion of lens 200 are contact surfaces 212-1, 212-2, 214-1, 214-2 joined with side restricting portions 114, 115 of the holding portion. In other words, notches that form contact surfaces 212-1, 212-2, 214-1, 214-2 are formed at the four corners, respectively, of the base portion.

Lens 200 shown in FIG. 9 may be replaced with a lens 200A with the increased light reflection efficiency. Lens 200A has a plurality of reflection planes 214 at prescribed sections on the side facing the substrate, on a plane opposite to a concave portion 203. Most of light beams radiating from the light emitting device accommodated in concave portion 210 are directly guided to convex portion 203. Of the rest of the light beams, light beams guided in a direction different from the optical axis are reflected at reflection planes 214. As a result, these light beams have their propagation direction changed and are guided toward the plane having convex portion 203 (light exit plane). The provision of such reflection planes 214 allows light radiating from the light emitting device to be emitted from the light exit plane more efficiently.

When lens 200A is attached to each of windows 102-1 to 102-8 of base 100, lens 200A is engaged with snap fits 111 (see FIG. 7 and FIG. 8) at contact surfaces 205-1 and 205-2 thereof. Lens 200A is also joined with bottom holding portions 112 and 113 of holding portion 110 at contact surfaces 209-1, 209-2, and 207 opposite to contact surfaces 205-1 and 205-2.

Lens 200A is also joined with side restricting portions 114 and 115 of the holding portion at contact surfaces 213-1, 213-2, 215-1, 215-2 formed at the notches at the four corners of lens 200A.

Lens 200A allows illumination light to be emitted efficiently, thereby increasing the illumination intensity. The increased illumination intensity (illumination efficiency) can improve the measurement accuracy, and in addition, the required illumination intensity can be achieved with less electricity, thereby suppressing power consumption and heat generation.

<<G. Details of Rigid Flexible Substrate>>

Referring now to FIG. 11 to FIG. 23, rigid flexible substrate 300 of illumination apparatus 1 in the present embodiment will be described.

[g1: Basic Structure]

Figure 11:
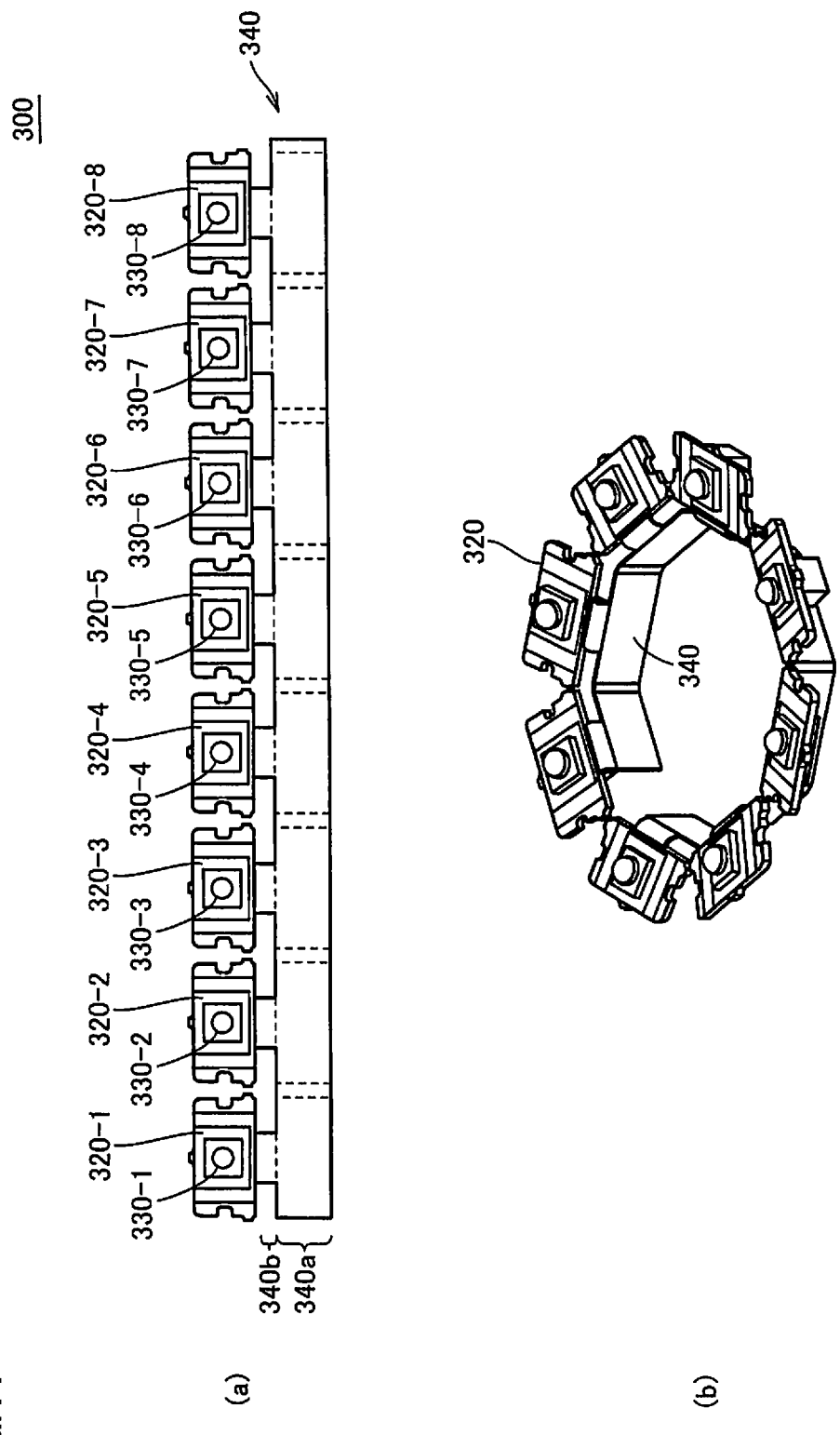
FIG. 11 is a diagram illustrating a configuration of a rigid flexible substrate of the illumination apparatus according to the embodiment of the present invention.
Figure 12:
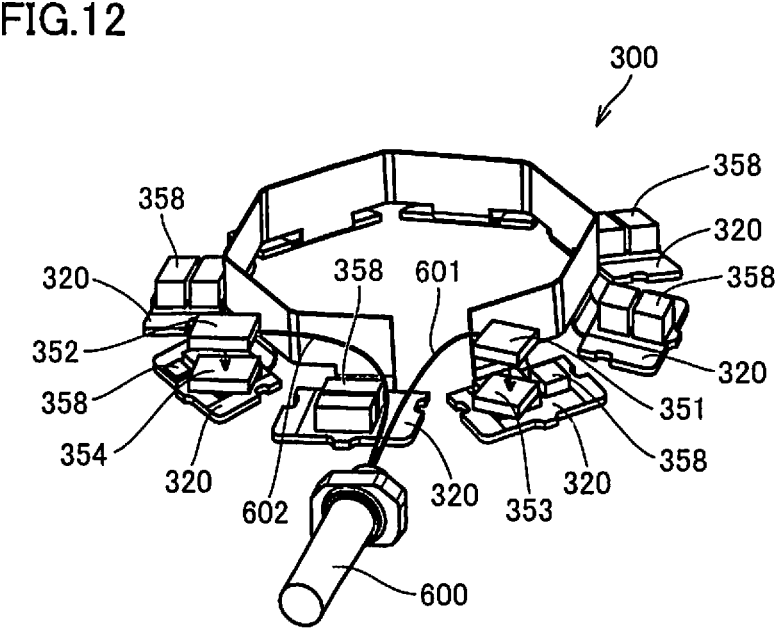
FIG. 12 is a diagram illustrating power feed to the rigid flexible substrate of the illumination apparatus according to the embodiment of the present invention.

FIG. 11 is a diagram illustrating a configuration of rigid flexible substrate 300 of illumination apparatus 1 according to the embodiment of the present invention. FIG. 11(a) shows rigid flexible substrate 300 immediately after production, and FIG. 11(b) shows rigid flexible substrate 300 before being installed into base 100. FIG. 12 is a diagram illustrating power feed to rigid flexible substrate 300 of illumination apparatus 1 according to the embodiment of the present invention.

Referring to FIG. 11(a), rigid flexible substrate 300 includes as many unit substrates 320-1 to 320-8 (which are also collectively referred to as "unit substrate 320") as lenses 200 attached to base 100. Each unit substrate 320-1 to 320-8 is formed as a body (rigid body) made of a relatively hard material for positioning and fixing as described above. Specifically, unit substrates 320-1 to 320-8 are made of glass epoxy substrates.

Light emitting devices 330-1 to 330-8 (which are also collectively referred to as "light emitting device 330") for generating light are mounted on the glass epoxy substrates (unit substrates 320-1 to 320-8), respectively. More specifically, light emitting device 330 is mounted at a prescribed position on unit substrate 320 by means of surface mounting or bare chip mounting. A micro-lens may be mounted in association with each light emitting device 330. More than one light emitting device may be mounted on each unit substrate 320, and the number of light emitting devices is set as appropriate according to the design value (illumination intensity) required for illumination apparatus 1.

With the use of such a rigid body substrate as unit substrate 320, the light emitting device can be positioned accurately with respect to the lens without deformation of the substrate even when being press-fitted and fixed to base 100.

Rigid flexible substrate 300 includes a flexible printed circuit board (hereinafter also referred to as "flexible substrate") 340 for electrical connection between unit substrates 320-1 to 320-8 (light emitting devices 330-1 to 330-8 mounted thereon). Flexible substrate 340 has wiring and the like for supplying power to light emitting device 330. More specifically, flexible substrate 340 has a conductor foil having a wiring pattern formed on a film-like insulator (base film) and covered with an insulator.

Illumination apparatus 1 is installed with unit substrate 320 that is the first substrate associated with each of a plurality of lenses 200 and accordingly disposed. Here, at least one light emitting device is mounted on each unit substrate 320. Illumination apparatus 1 is also installed with flexible substrate 340 for electrical connection between unit substrates 320 as the first substrates. Here, unit substrate 320 is configured as a rigid body, and flexible substrate 340 is configured to have flexibility.

Rigid flexible substrate 300 in this manner is formed in a concentric shape as shown in FIG. 11(b) and installed in base 100. In flexible substrate 340 of rigid flexible substrate 300, a portion 340a formed linearly across a plurality of unit substrates 320 and a portion 340b branching off from portion 340a toward each unit substrate 320 are integrally configured. Flexible substrate 340 is folded at points shown by the broken lines (see FIG. 11(a)) in the linearly formed portion 340a, whereby flexible substrate 340 is formed into an octagonal shape as shown in FIG. 11(b). Flexible substrate 340 is further folded circumferentially outward at points shown by the broken lines (see FIG. 11(a)) in portions 340b branching toward unit substrates 320, whereby unit substrates 320-1 to 320-8 are formed to have a predetermined angle relative to a flat plane defined by the generally round shape (octagonal shape) of flexible substrate 340. When flexible substrate 340 is bent, flexible substrate 340 is preferably shaped into a polygon as shown in FIG. 11(b) in relation with unit substrates 320. In this case, the points shown by the broken lines in FIG. 11(a) are preferably processed so as to facilitate the folding. Flexible substrate 340 may be bent in a round shape. In this case, folds at the points shown by the broken lines in FIG. 11(a) are not always necessary.

Because of a rigid body substrate used as unit substrate 320, unit substrate 320 is not deformed even in a state in which flexible substrate 340 is bent as shown in FIG. 11(b). Thus, light emitting device 330 surface-mounted on unit substrate 320 does not undergo stress, thereby preventing reduction in reliability.

In rigid flexible substrate 300 in this manner, flexible substrate 340 has a prescribed flat plane shaped along the circumferential direction of base 100, and each unit substrate 320 is bent at an angle corresponding to the inclination of lens 200 held in holding portion 110 of base 100, relative to the corresponding portion of flexible substrate 340 (portion 340a linearly formed across a plurality of unit substrates 320). In other words, flexible substrate 340 is bent in accordance with how the plurality of windows 102-1 to 102-8 are arranged.

As described later, flexible substrate 340 has a wiring pattern formed thereon such that light emitting devices 330-1 to 330-8 mounted on unit substrates 320-1 to 320-8 are connected in series. Therefore, a group of light emitting devices 330-1 to 330-8 can be driven to turn on by supplying power between two points on the wiring path formed by flexible substrate 340 including light emitting device 330s.

More specifically, as shown in FIG. 12, connectors 353 and 354 are mounted on two unit substrates 320, respectively, that are positioned in proximity to power supply cable 600 (power supply cable-through concave portion 150) penetrating base 100 and case 500 and thus introduced therein, among unit substrates 320 that configure rigid flexible substrate 300. Connectors 351 and 352 attached to the ends of wires 601 and 602 of positive and negative electrodes included in power supply cable 600 are connected to connectors 353 and 354.

Connectors 353 and 354 are oriented in non-parallel to both the longitudinal direction and the lateral direction of unit substrate 320. More specifically, the direction in which wires 601 and 602 are connected to connectors 353 and 354, respectively, is oriented toward power supply cable 600, in order to facilitate placement of wires 601 and 602 from power supply cable 600. In other words, flexible substrate 340 includes a pair of connectors 353 and 354 for electrical connection to power supply cable 600, and a pair of connectors 353 and 354 are provided in a direction corresponding to a position at which power supply cable 600 is introduced.

As described later, when there are a large number of light emitting devices 300 to turn on, such a configuration in that as many series-connected light emitting devices 330 as necessary are connected in parallel may be adopted.

A circuit component 358 for driving light emitting device 330 is mounted on that surface of each unit substrate 320 on which light emitting device 330 is not mounted. More specifically, a circuit component other than light emitting device 330 is basically mounted on a surface opposite to the surface on which light-emitting device 330 is mounted, in each unit substrate 320. Accordingly, the space efficiency is increased thereby reducing the substrate size of each unit substrate 320.

[g2: Facilitation of Assembly]

As described with reference to FIG. 3, rigid flexible substrate 300 is formed in a concentric shape and is then inserted between base 100 corresponding to the first casing and case 500 corresponding to the second casing. During installation into the case in this manner, flexible substrate 340 in a bent state may be deformed to slip in between base 100 corresponding to the first casing and case 500 corresponding to the second casing. In other words, flexible substrate 340 may fall inward or outward from the original position thereby interfering with base 100 or case 500.

Then, the assembly performance can be improved by using an auxiliary fixing member as shown in FIG. 13.

FIG. 13 is a diagram illustrating an auxiliary fixing member attached to the rigid flexible substrate of the illumination apparatus according to the embodiment of the present invention. FIG. 13(a) shows a state in which a ring-shaped member 360 serving as an auxiliary fixing member has been attached to rigid flexible substrate 300 formed in a concentric shape, and FIG. 13(b) shows a state in which ring-shaped member 360 serving as an auxiliary fixing member is to be attached to rigid flexible substrate 300 formed in a concentric shape.

As shown in FIG. 13(b), ring-shaped member 360 is adopted as an auxiliary fixing member. The inner diameter of ring-shaped member 360 is designed to be larger than a circumcircle of flexible substrate 340 formed in a concentric shape by a prescribed margin. Ring-shaped member 360 is then attached on the outer circumference of flexible substrate 340 formed in a concentric shape. Ring-shaped member 360 is preferably formed of a material such as resin.

Flexible substrate 340 is supported by ring-shaped member 360 in this way, whereby deformation (falling inward or outward from the original position) of flexible substrate 340 can be prevented. Accordingly, slippage of flexible substrate 340 in between base 100 corresponding to the first casing and case 500 corresponding to the second casing can be avoided. As a result, the assembly performance can be improved.

[g3. Wiring Pattern]

An example of wiring pattern on the rigid flexible substrate will now be described.

Figure 14:
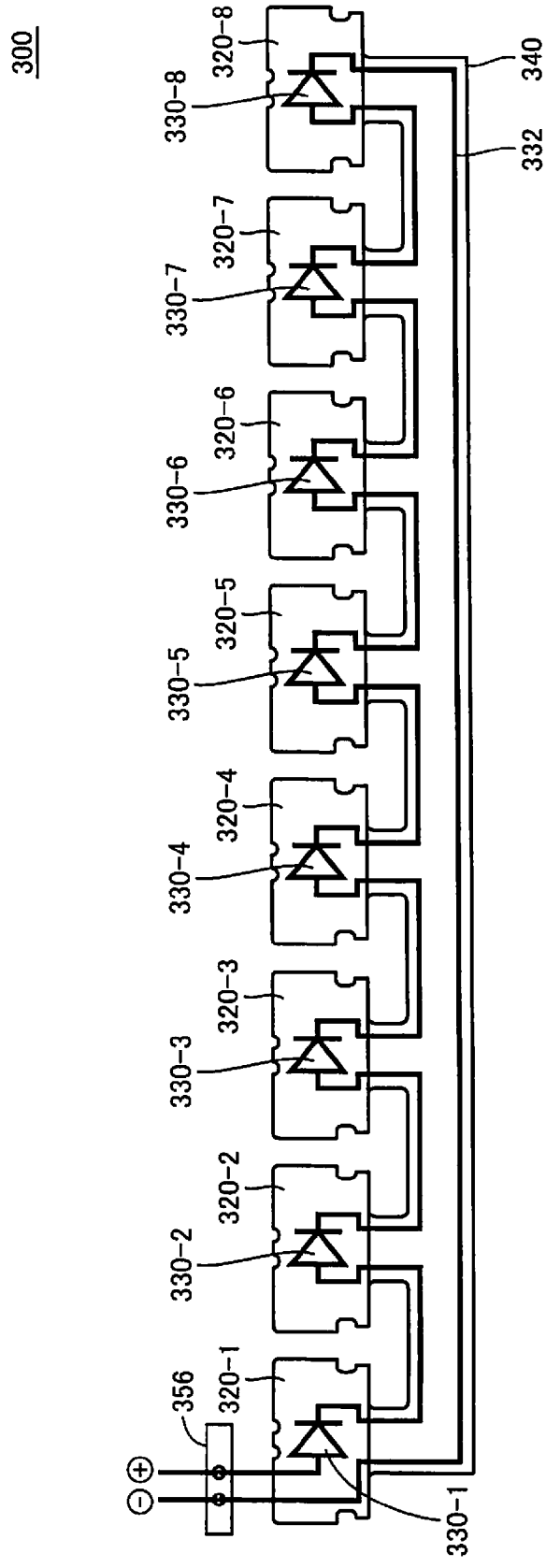
FIG. 14 is a diagram illustrating an exemplary wiring pattern on the rigid flexible substrate of the illumination apparatus according to the embodiment of the present invention.
Figure 15:
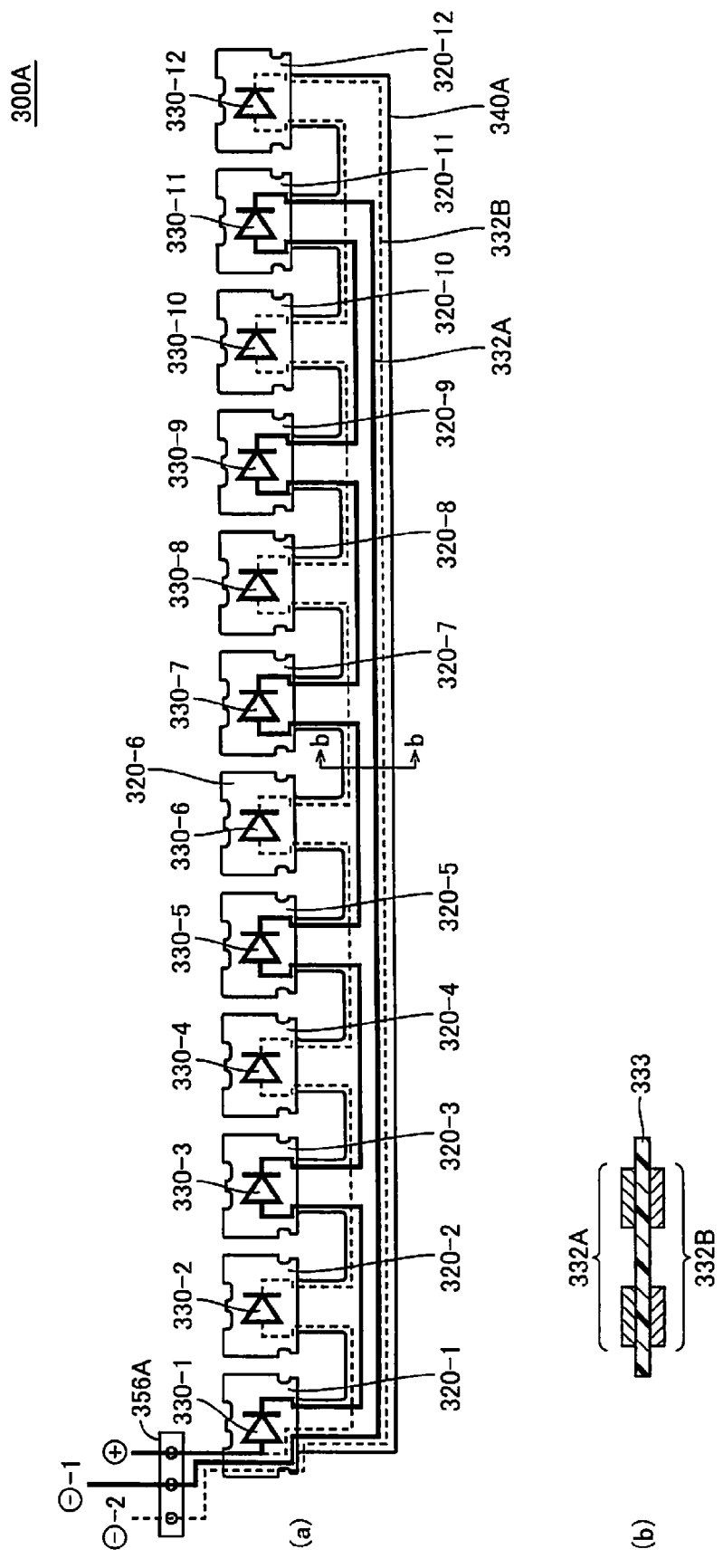
FIG. 15 is a diagram illustrating an exemplary wiring pattern on the rigid flexible substrate of the illumination apparatus according to the embodiment of the present invention.

FIG. 14 and FIG. 15 are diagrams illustrating an example of the wiring pattern on the rigid flexible substrate of the illumination apparatus according to the embodiment of the present invention. FIG. 14 shows an example in which eight light emitting devices 330 are mounted on one rigid flexible substrate, and FIG. 15 shows an example in which twelve light emitting devices 330 are mounted on one rigid flexible substrate. In particular, FIG. 14 and FIG. 15 show an exemplary configuration that allows the connectors for power supply to be unified into one.

In rigid flexible substrate 300 shown in FIG. 14, a supply line 332, which connects light emitting devices 330-1 to 330-8 mounted on unit substrates 320-1 to 320-8, respectively, in series, is formed on flexible substrate 340. The opposite ends of supply line 332 are both connected to a connector 356 and then connected to a controller for turning on light emitting devices 330 through connector 356 as described later. One end of supply line 332 is supplied with positive potential through connector 356, and the other end of supply line 332 is supplied with negative potential through connector 356.

In a rigid flexible substrate 300A shown in FIG. 15, two supply lines 332A and 332B are used for twelve light emitting devices to supply power to six in parallel each. Specifically, power supply line 332A shown by the solid line in FIG. 15 is formed to connect the odd-numbered unit substrates 320-1, 320-3, 320-5, 320-7, 320-9, and 320-11 in series, whereas power supply line 332B shown by the broken line in FIG. 15 is formed to connect the even-numbered unit substrates 320-2, 320-4, 320-6, 320-8, 320-10, and 320-12 in series.

As described later, since control is performed such that a constant current at a prescribed magnitude is supplied to light emitting devices 330, supply lines 332A and 332B have supply current controlled independently from each other such that the magnitude of currents flowing through the supply lines does not vary. In order to do so, positive potential is supplied commonly to one ends of supply lines 332A and 332B through connector 356A, whereas the respective other ends of supply lines 332A and 332B are connected to different negative potential terminals through connector 356A.

Supply line 332A and supply line 332B cannot cross each other with isolation being kept on flexible substrate 340. Therefore, in general, supply line 332A is formed on one surface of flexible substrate 340 and supply line 332B is formed on the other surface of flexible substrate 340. This example is shown in FIG. 15(b).

[g4: First Modification]

As the configuration of the rigid flexible substrate, configurations as shown in FIG. 16 to FIG. 19 may be adopted in place of the manner shown in FIG. 11 to FIG. 15 as described above.

Figure 16:
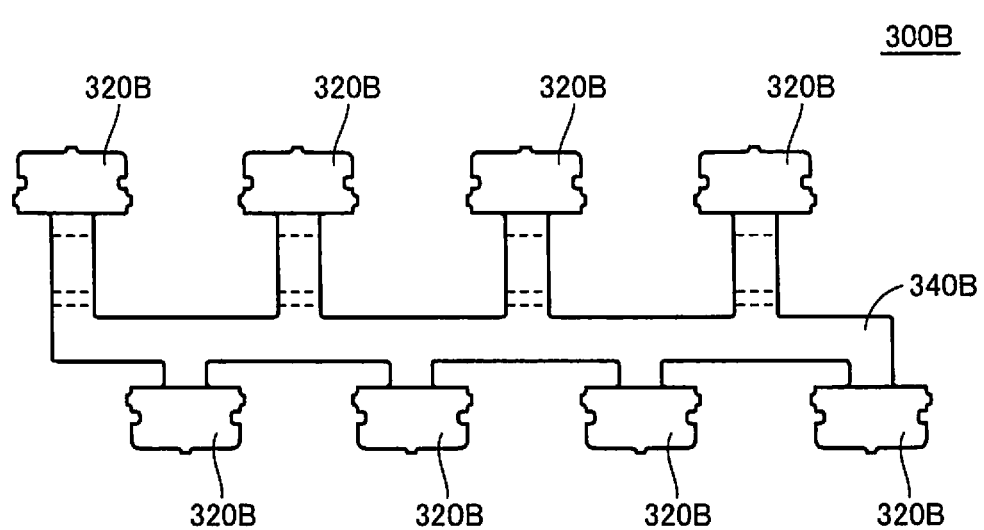
FIG. 16 is a diagram showing a modification of the rigid flexible substrate of the illumination apparatus according to the embodiment of the present invention.
Figure 18:
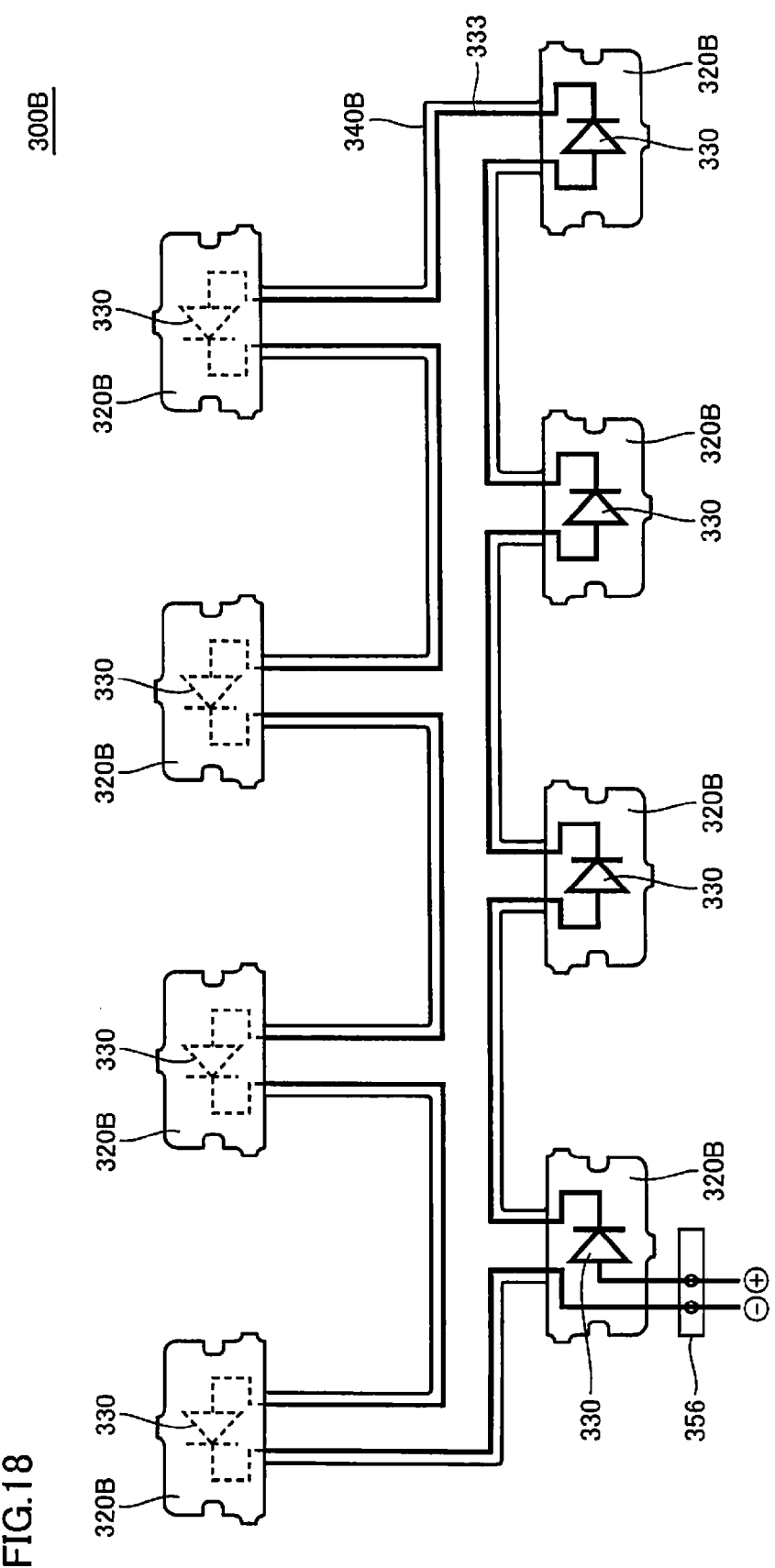
FIG. 18 is a diagram illustrating an exemplary wiring pattern in the modification of the rigid flexible substrate of the illumination apparatus according to the embodiment of the present invention.
Figure 19:
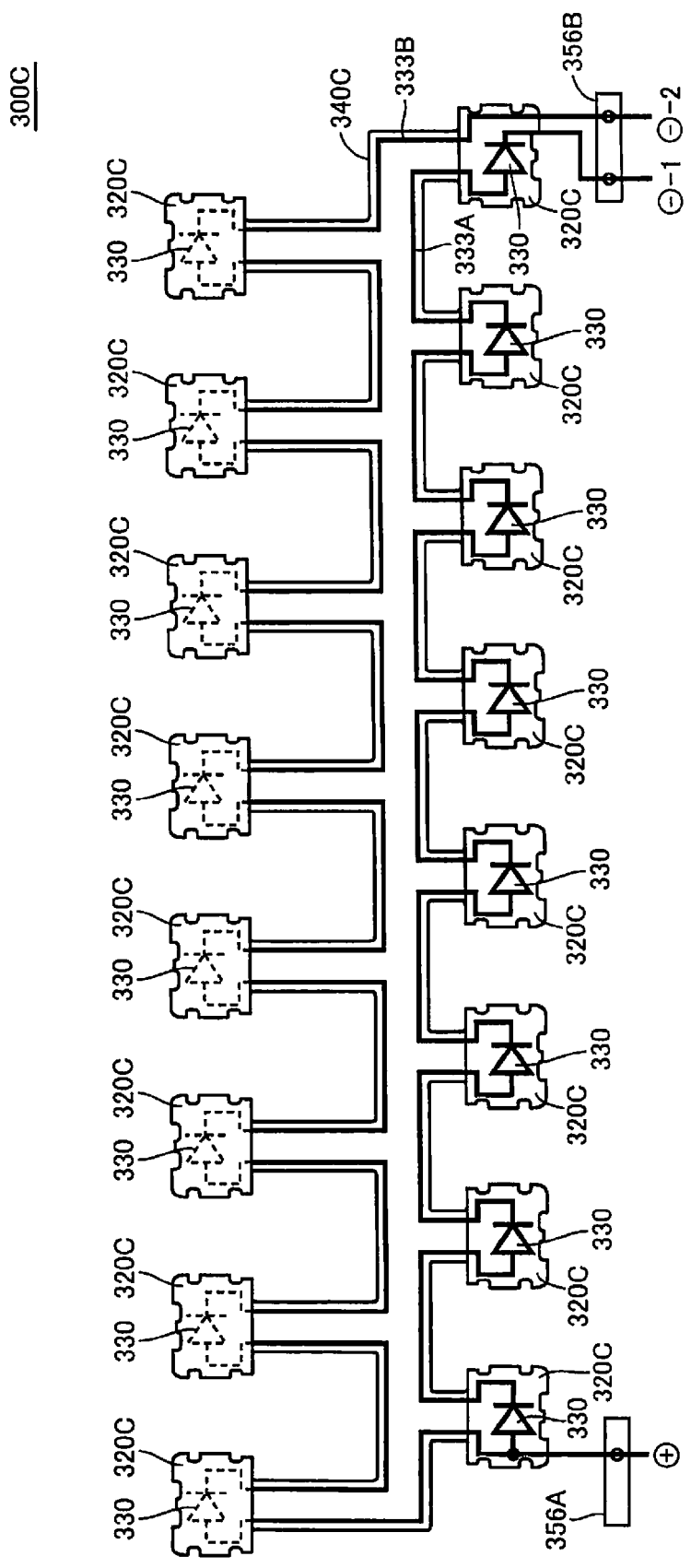
FIG. 19 is a diagram illustrating an exemplary wiring pattern in a modification of the rigid flexible substrate of the illumination apparatus according to the embodiment of the present invention.

FIG. 16 is a diagram showing a modification of the rigid flexible substrate of illumination apparatus 1 according to the embodiment of the present invention. FIG. 17 is a diagram illustrating an auxiliary fixing member attached to the modification of the rigid flexible substrate of illumination apparatus 1 according to the embodiment of the present invention. FIG. 18 and FIG. 19 are diagrams illustrating an example of the wiring pattern in the modification of the rigid flexible substrate of the illumination apparatus according to the embodiment of the present invention.

Referring to FIG. 16, a rigid flexible substrate 300B is configured such that unit substrates 320A each having light emitting device 330 mounted thereon are disposed in a staggered pattern (alternately disposed on opposite sides). These unit substrates 320B are connected through a flexible substrate 340B. Rigid flexible substrate 300B can also be configured in a shape suitable for installation in base 100 as shown in FIG. 12 by folding flexible substrate 340B as appropriate.

More specifically, that portion of flexible substrate 340B which is connected to unit substrates 320B disposed on the upper side in the figure is longer relative to that portion of flexible substrate 340B which is connected to unit substrates 320B disposed on the lower side in the figure. Then, unit substrates 320B disposed on the upper side in the figure are folded in the upward and downward directions in the figure, whereby a similar structure as rigid flexible substrate 300 shown in FIG. 11(*a*) is implemented. Specifically, four unit substrates 320B disposed on the upper side in the figure are folded at the positions shown by the broken lines, and flexible substrate 340B is then bent into a generally round shape (octagonal shape). Therefore, in flexible substrate 340B, the plane on which light emitting devices 330 are mounted on unit substrates 320B on the upper side in the figure is opposite to the plane on which light emitting devices 330 are mounted on unit substrates 320B on the upper side in the figure.

More specifically, as shown in FIG. 17, of rigid flexible substrates 300B, four unit substrates 320B (those positioned on the upper side in the figure in FIG. 16) are folded circumferentially outward and then formed into a ring shape. In this modification, preferably, an auxiliary fixing member as shown in FIG. 17(*b*) is also used in order to improve the assembly performance. A ring-shaped member 360B shown in FIG. 17(*b*) is basically similar to ring-shaped member 360 shown in FIG. 13(*b*), except that notches 3601 are provided at positions corresponding to the four rigid flexible substrates 300B folded circumferentially outward. Notch 3601 is a portion for absorbing the thickness produced by folding flexible substrate 340B.

Finally, ring-shaped member 360B that is an auxiliary fixing member is attached to rigid flexible substrate 300B formed in a concentric shape as shown in FIG. 17(*a*) and is then installed in the case.

With the configuration as described above, the pitch of the unit substrates can be made narrower when compared with the configuration (one-side arrangement) in which the unit substrates are disposed on one side in the longitudinal direction of flexible substrate 340 as shown in FIG. 11, so that the ring diameter of the final illumination apparatus 1 can be reduced. In addition, the rigid flexible substrate per se can be reduced in size.

Referring now to FIG. 18 and FIG. 19, examples of the wiring pattern in rigid flexible substrate 300B are illustrated. FIG. 18 shows an example in which eight light emitting devices 330 are mounted on one rigid flexible substrate, and FIG. 19 shows an example in which sixteen light emitting devices 330 are mounted on one rigid flexible substrate.

In rigid flexible substrate 300B shown in FIG. 18, a supply line 333 is formed on flexible substrate 340B to connect eight light emitting devices 330 mounted on eight unit substrates 320B, respectively, in series. The opposite ends of supply line 333 are both connected to connector 356 and further connected to a controller for turning on light emitting devices 330 as described later through connector 356. Specifically, one end of supply line 333 is supplied with positive potential through connector 356 and the other end of supply line 333 is supplied with negative potential through connector 356.

In a rigid flexible substrate 300C shown in FIG. 19, two supply lines 333A and 333B are used to supply power to sixteen light emitting devices 330, eight in parallel each, so that the voltage applied to the supply lines does not become excessively high. Supply line 333A is formed to connect unit substrates 320C disposed on the lower side in the figure in series, and supply line 333B is formed to connect unit substrates 320C disposed on the upper side in the figure in series.

As described later, since control is performed such that constant current at a prescribed magnitude is supplied to light emitting devices 330, supply lines 333A and 333B have supply currents controlled independently from each other so that the magnitude of currents flowing through the supply lines does not vary. In order to do so, one ends of supply lines 333A and 333B are supplied with positive potential through connector 356A, whereas the other ends of supply lines 333A and 333B are connected to different, negative potential terminals through connector 356B.

In rigid flexible substrate 300C shown in FIG. 19, supply line 333A and supply line 333B can be formed without crossing each other, so that two supply lines 333A and 333B can be formed on one surface of flexible substrate 340.

[g5: Second Modification]

Figure 20:
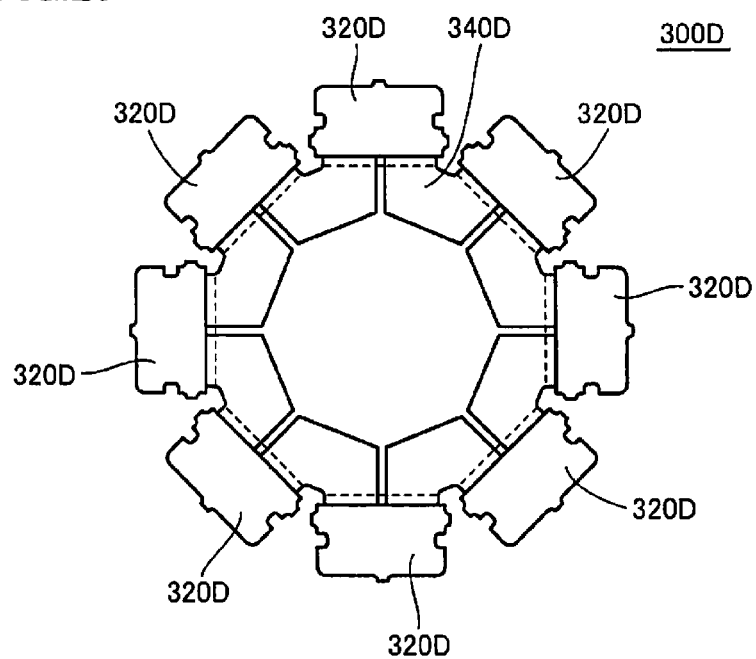
FIG. 20 is a diagram showing a modification of the rigid flexible substrate of the illumination apparatus according to the embodiment of the present invention.

FIG. 20 is a diagram showing a modification of the rigid flexible substrate of the illumination apparatus according to the embodiment of the present invention. Referring to FIG. 20, a rigid flexible substrate 300D is configured such that unit substrates 320D each having a light emitting device mounted thereon are concentrically (radially) disposed. In rigid flexible substrate 300D shown in FIG. 20, a flexible substrate 340D is arranged on the center side, and unit substrates 320D are disposed on the outer circumferential side. Each unit substrate 320D is electrically connected to unit substrate 320D positioned adjacent thereto through flexible substrate 340D. This rigid flexible substrate 300D can also be configured in a shape suitable for installation in base 100 as shown in FIG. 12 by folding flexible substrate 340D as appropriate.

[g6: Third Modification]

Figure 21:
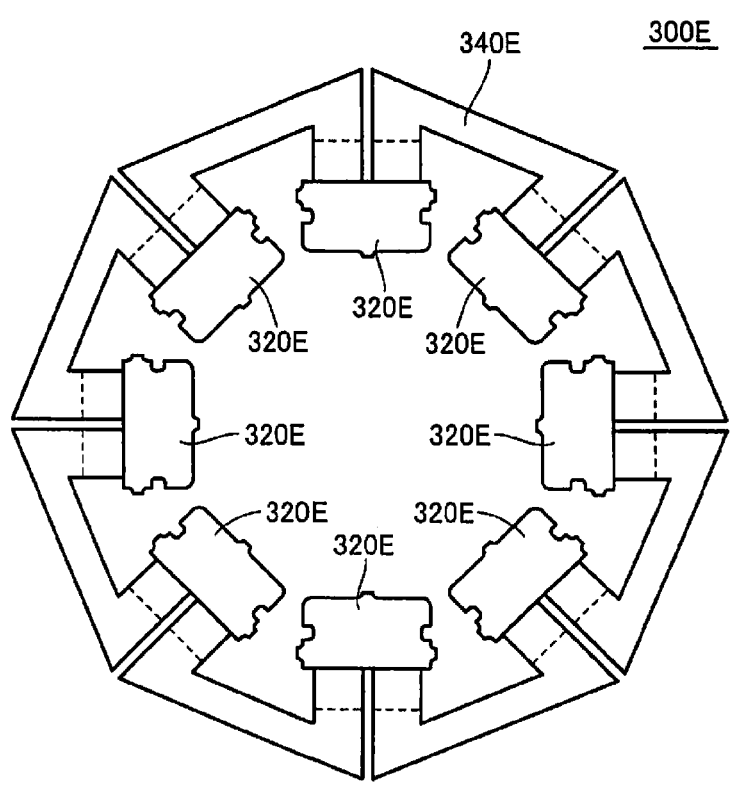
FIG. 21 is a diagram showing a modification of the rigid flexible substrate of the illumination apparatus according to the embodiment of the present invention.

FIG. 21 is a diagram showing a modification of the rigid flexible substrate of the illumination apparatus according to the embodiment of the present invention. Referring to FIG. 21, a rigid flexible substrate 300E is configured such that unit substrates 320E each having a light emitting device mounted thereon are concentrically (radially) disposed in a similar manner as rigid flexible substrate 300D shown in FIG. 20. However, in rigid flexible substrate 300E shown in FIG. 21, a flexible substrate 340E is positioned on the outer circumferential side, and unit substrate 320E are positioned on the inner circumferential side.

Each unit substrate 320E is electrically connected to unit substrates 320E positioned adjacent thereto through flexible substrate 340E. This rigid flexible substrate 300E can also be configured in a shape suitable for installation in base 100 as shown in FIG. 12 by folding flexible substrate 340E as appropriate.

[g7: Fourth Modification]

Figure 22:
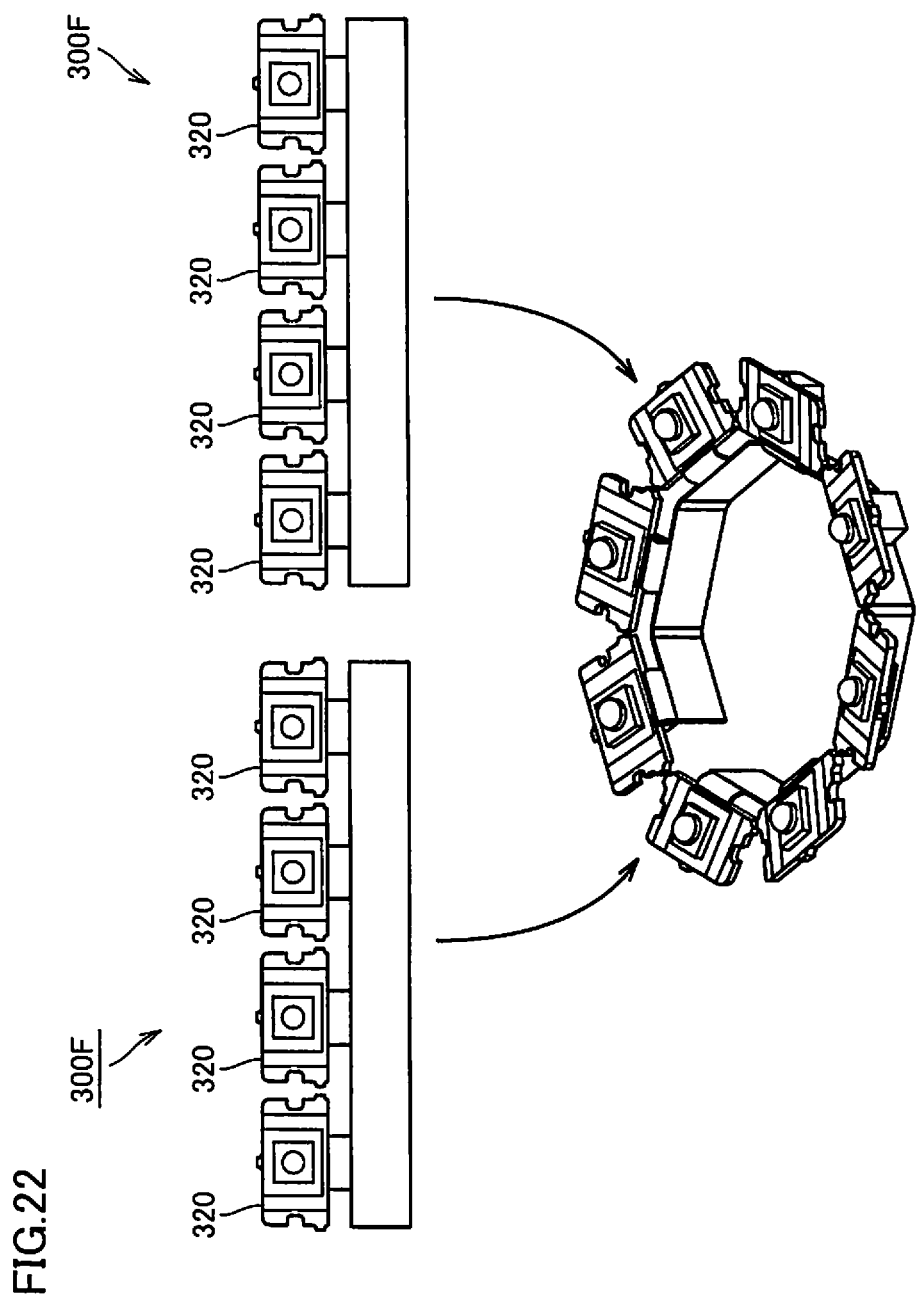
FIG. 22 is a diagram showing a modification of the rigid flexible substrate of the illumination apparatus according to the embodiment of the present invention.

FIG. 22 is a diagram showing a modification of the rigid flexible substrate of the illumination apparatus according to the embodiment of the present invention. Referring to FIG.

22, a plurality of rigid flexible substrates 300F may be combined to configure a ring shape in which light emitting devices are concentrically formed. For example, as shown in FIG. 22, rigid flexible substrate 300F including four unit substrates 320 is bent to form part (semicircle) of a generally round shape (octagonal shape), and two sets of such rigid flexible substrates 300F are combined to configure an illumination module having the light emitting devices configured in a ring shape.

With this method in which a plurality of rigid flexible substrates, each having fewer unit substrates 320, are combined, the kinds of rigid flexible substrate can be reduced even when a lineup of many variations (products) is offered.

[g8: Manner of Mounting Light Emitting Device]

In the illumination apparatus in the present embodiment, light emitting device 330 is mounted on unit substrate 320. Light emitting device 330 is typically a chip LED. When mounting such a chip LED, it is preferable to adopt a manner of mounting as described below in order to prevent degradation due to heat generated from the chip LED itself.

Figure 23:
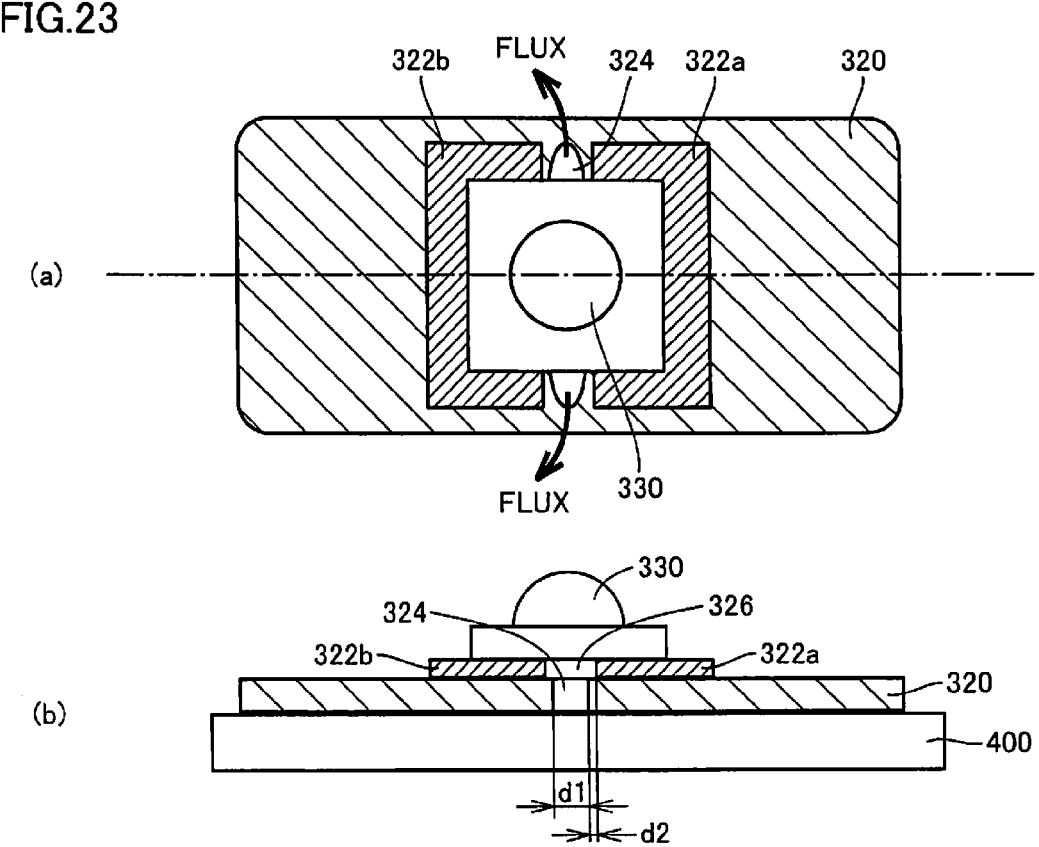
FIG. 23 is a diagram illustrating an exemplary manner of mounting a light emitting device of the illumination apparatus according to the embodiment of the present invention.

FIG. 23 is a diagram illustrating an exemplary manner of mounting a light emitting device of the illumination apparatus according to the embodiment of the present invention. Referring to FIG. 23, light emitting device 330 is disposed on lands 322a and 322b formed on unit substrate 320. Lands 322a and 322b correspond to electrodes (pads) for supplying positive potential and negative potential, respectively.

Lands 322a and 322b are disposed to be spaced apart from each other by a prescribed distance. In illumination apparatus 1 in the present embodiment, a hole 324 is formed for discharging flux in a region corresponding to the gap between lands 322a and 322b on unit substrate 320. The flux is a component included in solder used when light emitting device 330 is mounted on lands 322a and 322b. It is difficult to remove the flux during the production process.

When a voltage supplied to light emitting device 330 is applied with the gap between lands 322a and 322b being filled with a volatile component of flux and when exposed in a high-temperature environment due to heat generated by light emitting device 330, solder for electrical connection between light emitting device 330 and lands 322a and 322b moves on the land surface or on the unit substrate surface. The movement of solder causes dendrite. The generated dendrite causes poor isolation between lands 322a and 322b.

Then, in unit substrate 320 of illumination apparatus 1 in the present embodiment, hole 324 (slit or dent) for releasing flux (its volatile component) which cannot be completely removed in the production process is provided between the lands on unit substrate 320.

Hole 324 is provided mainly for the purpose of preventing the space formed by light emitting device 330 from being filled with the flux. Therefore, the length in the longitudinal direction of hole 324 is preferably set in such a degree that hole 324 is partially exposed from light emitting device 330 on unit substrate 320 as viewed from above. In other words, it is preferable that hole 324 is not entirely covered with light emitting device 330 on unit substrate 320 as viewed from above.

Because of such a configuration, even when the bottom surface side of unit substrate 320 is covered with heat sink sheet 400 or the like, flux can be sufficiently released in the direction of the top surface. It is preferable to provide a sufficient space between hole 324 and the end of unit substrate 320 in order to prevent distortion of unit substrate 320.

As a typical example of mounting, the thickness of lands 322a and 322b is about 18 μm, and a width d1 of hole 324 in the lateral direction is about 0.8 mm. The width of a gap 326 between land 322a and 322b is about 1 mm. The difference d2 between the width d1 of gap 326 and the width of gap 326 is about 0.1 mm, which is a space for preventing separation of a pad formed on the bottom surface of light emitting device 330.

By mounting light emitting device 330 in this manner, the effect of flux left during the mounting process can be reduced. As a result, the reliability of the illumination apparatus in the present embodiment can be improved.

<<H. Details of Heat Sink Sheet>>

Figure 24:
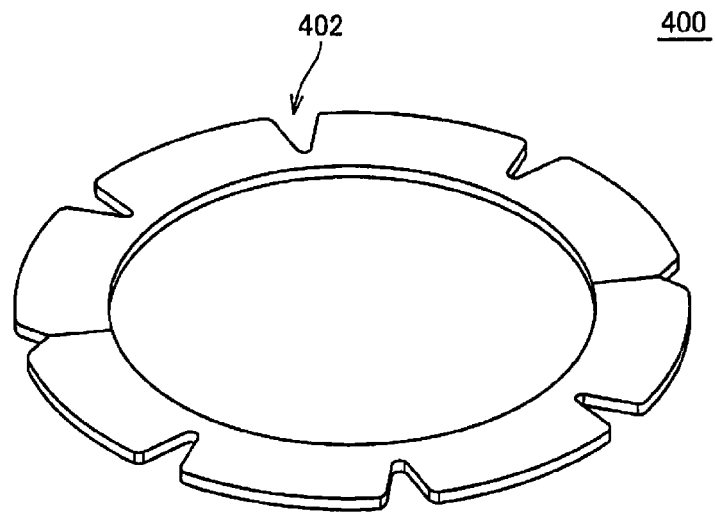
FIG. 24 is a diagram illustrating a configuration of a heat sink sheet of the illumination apparatus according to the embodiment of the present invention.

Referring now to FIG. 24, heat sink sheet 400 of illumination apparatus 1 in the present embodiment will be described.

FIG. 24 is a diagram illustrating a configuration of heat sink sheet 400 of illumination apparatus 1 according to the embodiment of the present invention. Referring to FIG. 24, heat sink sheet 400 basically prevents the periphery of light emitting device 330 from being heated, by transmitting heat generated from light emitting device 330 associated with lens 200 and accordingly disposed. More specifically, heat sink sheet 400 is a sheet based on silicone gel and has a relatively high thermal conductivity. Heat sink sheet 400 is flexible and has a separator and a releasing film formed on the surface thereof. In other words, heat sink sheet 400 fits well on concave and convex surfaces. Using this characteristic, heat sink sheet 400 also functions as a cushion member or a pressing portion for lens 200 and rigid flexible substrate 300 (light emitting device 330) inserted into a space between base 100 and case 500. In short, heat sink sheet 400 is a heat conducting and elastic sheet inserted between unit substrate 320 and the pressing portion of case 500.

In order to achieve the object as described above, heat sink sheet 400 has such a shape that at least covers the position of unit substrate 320 included in rigid flexible substrate 300 attached to base 100.

In illumination apparatus 1 in the present embodiment, lens 200 and unit substrate 320 (light emitting device 330) are positioned at a prescribed angle relative to the center axis (optical axis AXC) of center hole 700, and therefore, the surfaces of unit substrates 320 are not present on the same plane. Specifically, the back surfaces of unit substrates 320 are formed in a concave shape corresponding to the radiation plane of illumination apparatus 1.

Therefore, heat sink sheet 400 is provided with cuts 402 every prescribed angles so as to be closely adhered on such a non-flat plane. Because of cuts 402, heat sink sheet 400 can easily be deformed as a whole into a concave shape, thereby increasing the close adhesion with light emitting device 330. More specifically, heat sink sheet 400 includes a plurality of pieces corresponding to the respective unit substrates 320 as divided by cuts 402. In other words, heat sink sheet 400 is generally round and has cuts 402 and is thus sectioned to correspond to how unit substrates 320 are arranged.

<<I. Details of Case>>

Figure 25:
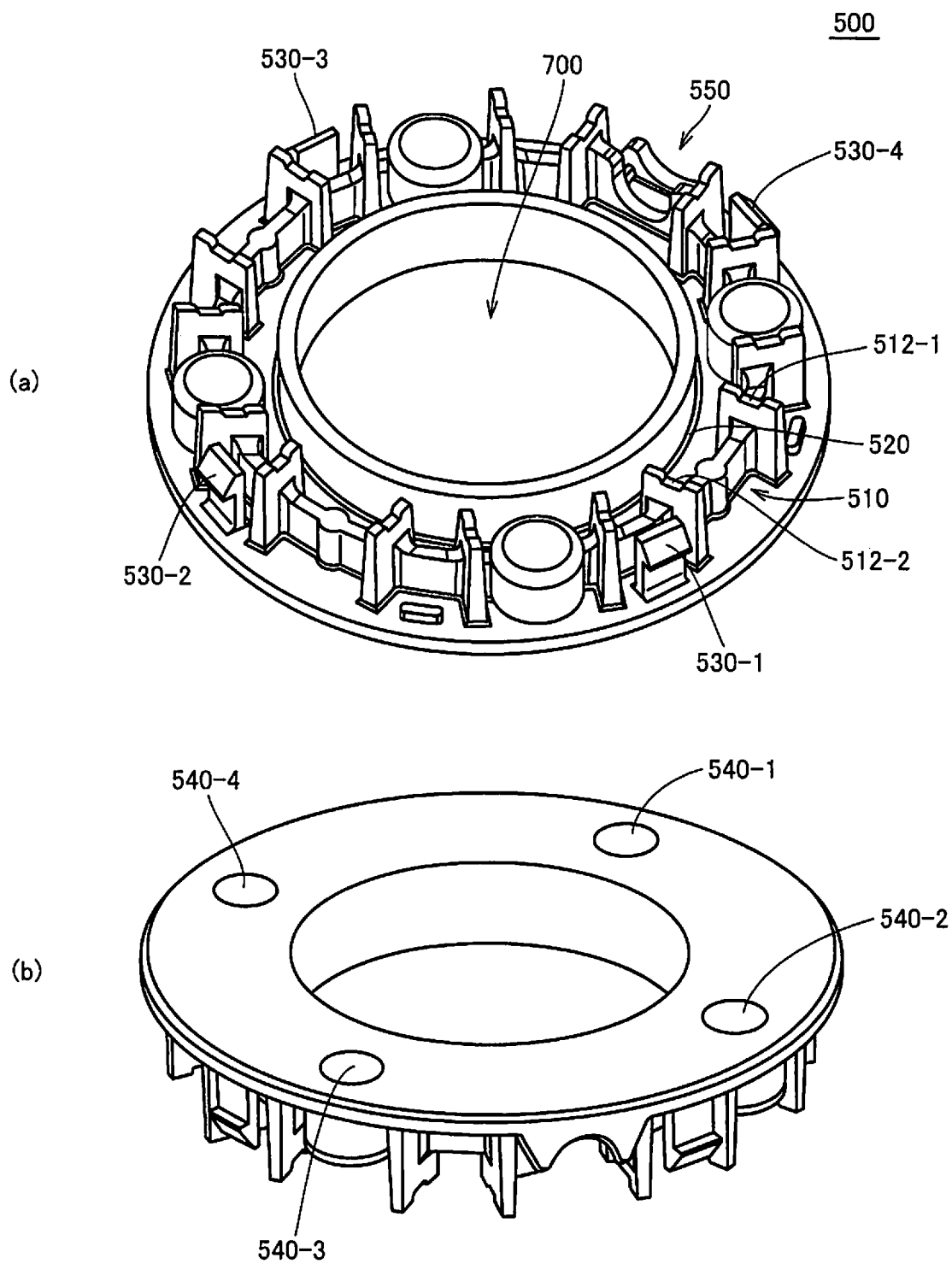
FIG. 25 is a perspective view showing an appearance of a case of the illumination apparatus according to the embodiment of the present invention.

Referring now to FIG. 25, case 500 of illumination apparatus 1 in the present embodiment will be described.

FIG. 25 is a perspective view showing an appearance of case 500 of illumination apparatus 1 according to the embodiment of the present invention. Specifically, FIG. 25(a) represents the side facing the radiation plane of case 500, and FIG. 25(b) represents the back side of case 500.

As shown in FIG. 25(a), case 500 is provided with a holding/restraining portion for positioning lens 200 and rigid flexible substrate 300 (strictly speaking, light emitting device 330 mounted on unit substrate 320) with respect to base 100, as described above. More specifically, case 500 is provided with a pair of pressing portions 512-1 and 512-2 for each of a plurality of lenses 200 (light emitting devices 330). When base 100 is engaged with case 500, the pair of pressing portions 512-1 and 512-2 presses the opposite ends of the corresponding unit substrate 320. Thus, pressing portions 512-1 and 512-2 press the corresponding unit substrate 320 at opposite ends thereof for positioning and fixing with respect to base 100.

More specifically, the contact surfaces (pressing surfaces) of pressing portions 512-1 and 512-2 are parallel to the positioning surfaces of base 100 with respect to the direction of the optical axis of the lens. In other words, pressing portions 512-1 and 512-2 push lens 200 and unit substrate 320 in the direction parallel to the corresponding radiation plane of illumination apparatus 1. In short, case 500 includes pressing portion 512-1 and 512-2 for pressing each unit substrate 320 attached to base 100 toward the radiation plane when case 500 is coupled with base 100.

The size (the length in the direction of the optical axis) of pressing portions 512-1 and 512-2 is determined in consideration of the thickness of heat sink sheet 400 and the like since heat sink sheet 400 is inserted between unit substrate 320 and case 500.

Preferably, a clearance smaller than the thickness of heat sink sheet 400 is provided between unit substrate 320 and pressing portions 512-1, 512-2 in a state in which base 100 and case 500 are integrated together.

Figure 26:
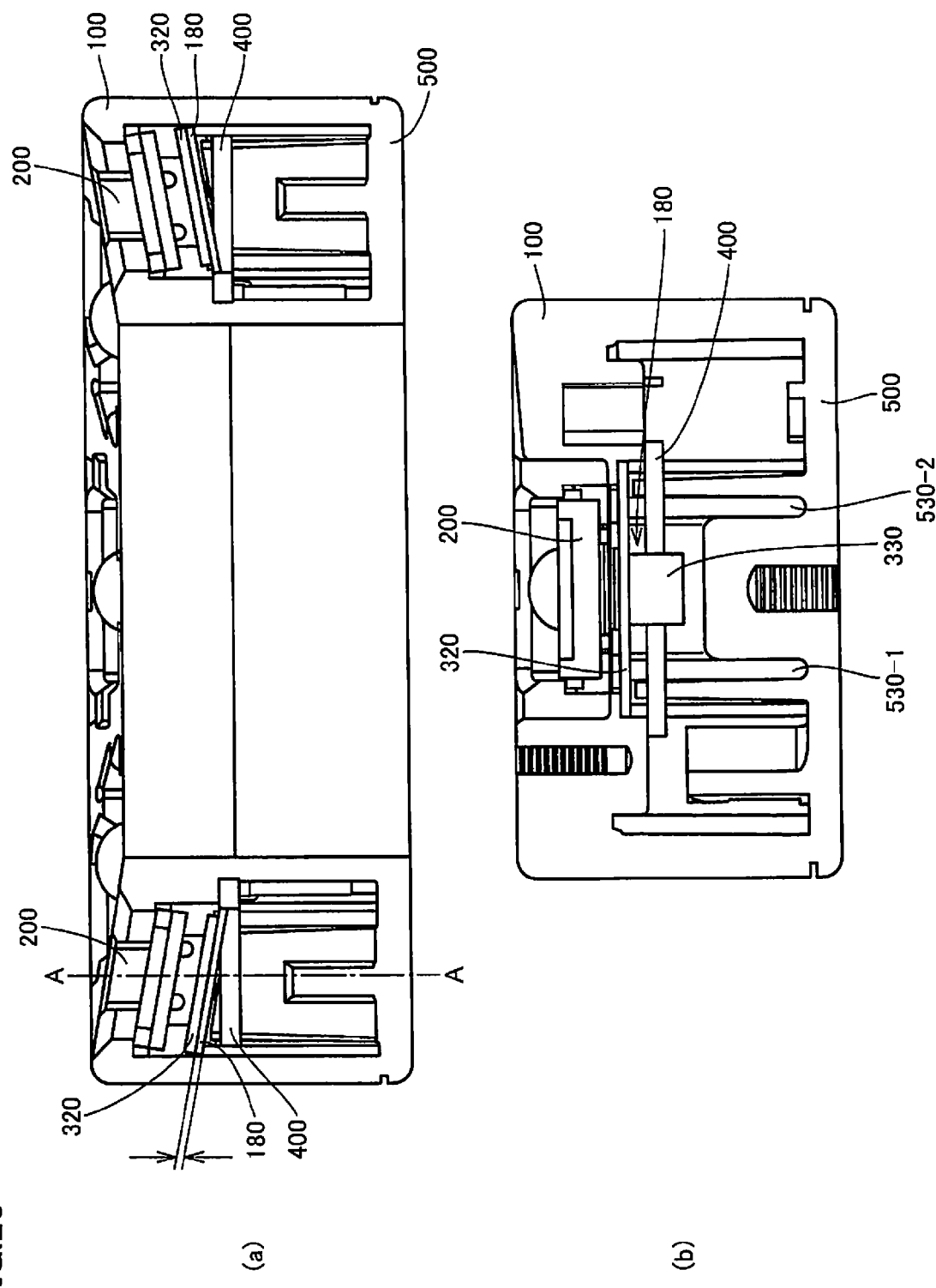
FIG. 26 is a cross-sectional view in a state in which the illumination apparatus according to the embodiment of the present invention is integrated.

FIG. 26 is a cross-sectional view in a state in which illumination apparatus 1 according to the embodiment of the present invention is integrated. Here, FIG. 26(a) shows a cross section of illumination apparatus 1 cut along the radial direction, and FIG. 26(b) shows a cross section of illumination apparatus 1 cut along the circumferential direction (the broken line A-A shown in FIG. 26(a)).

Referring to FIG. 26, first, the pressure from pressing portions 512-1 and 512-2 and the like elastically deforms heat sink sheet 400 and presses heat sink sheet 400 against unit substrate 320, so that the dimensional tolerances of base 100 and case 500 are absorbed. At the same time, lens 200 and unit substrate 320 are fixed, and heat is dissipated from unit substrate 320.

Here, a clearance 180 smaller than the thickness of heat sink sheet 400 is preferably provided between unit substrate 320 and pressing portions 512-1, 512-2 in the state in which base 100 and case 500 are integrated together. Here, light emitting device 330 mounted on unit substrate 320 and a component such as a circuit for driving light emitting device 330 are preferably disposed between pressing portion 512-1 and pressing portion 512-2. Therefore, pressing portions 512-1, 512-2 are configured to come into contact with the opposite ends of the corresponding unit substrate 320.

Case 500 is provided with an accommodation space 520 for accommodating flexible substrate 340 of rigid flexible substrate 300. More specifically, rigid flexible substrate 300 is inserted into base 100 in the state in which flexible substrate 340 is formed in a octagonal shape and unit substrates 320 are folded circumferentially outward as shown in FIG. 11. Flexible substrate 340 formed in a octagonal shape of rigid flexible substrate 300 is accommodated in accommodation space 520 formed along a member that forms the inner circumferential surface.

The outer circumferential surface of case 500 is partially notched to provide a power supply cable-through concave portion 550 for introducing power supply cable 600 into case 500. Power supply cable-through concave portion 150 of base 100 shown in FIG. 6 and power supply cable-through concave portion 550 of case 500 shown in FIG. 25 are combined to form a round hole through which power supply cable 600 passes.

On the back side of case 500, screw holes 540-1 to 540-4 are provided for fixing illumination apparatus 1 to a fixture or the like.

Base 100 and case 500 are engaged with each other using snap fits and thus integrated together. More specifically, case 500 is provided with fitting pawls 530-1 to 530-4 of the snap fits, which are fitted in the corresponding fitting holes 130-1 to 130-4 of base 100, whereby case 500 is positioned with respect to base 100.

<<J. Variations of Illumination Apparatus>>

In the foregoing description, illumination apparatus 1 having eight lenses attached on the radiation plane are mainly illustrated. These configurations can be replaced with a configuration having more lenses or fewer lenses.

Figure 28:
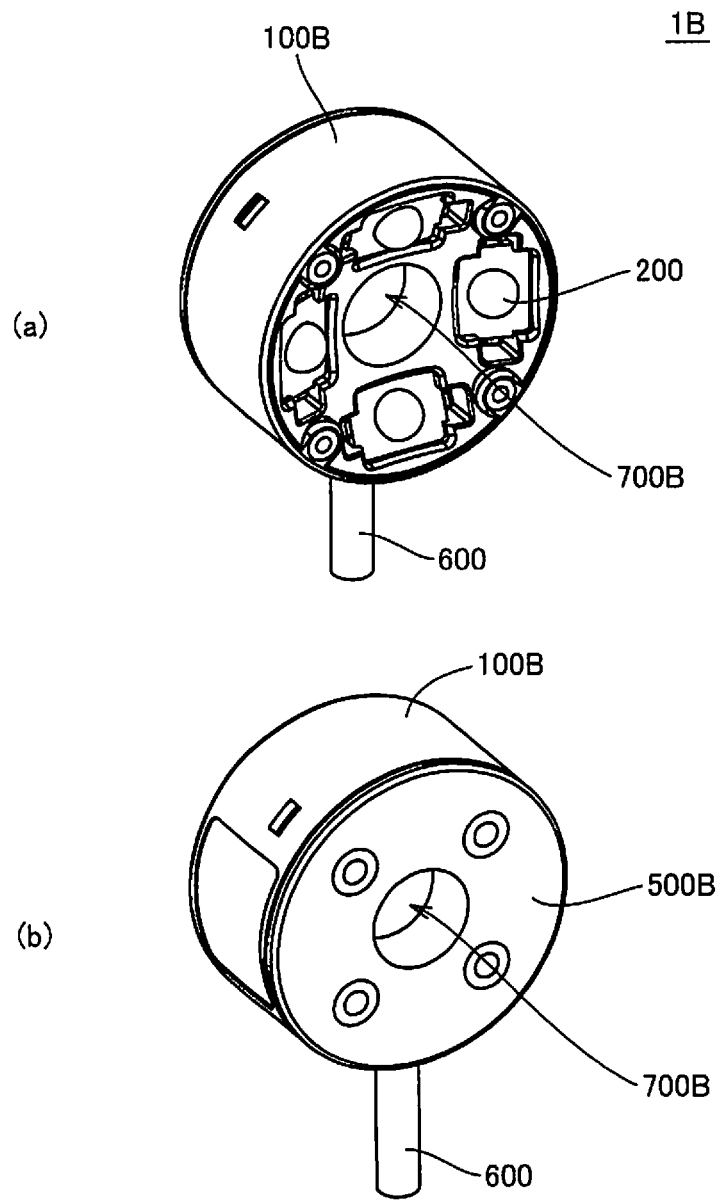
FIG. 28 is a perspective view showing an appearance of the illumination apparatus according to another modification of the embodiment of the present invention.

FIG. 27 is a perspective view showing an appearance of an illumination apparatus 1A according to a modification of the embodiment of the present invention. FIG. 28 is a perspective view showing an appearance of an illumination apparatus 1B according to another modification of the embodiment of the present invention. Here, FIG. 27(a) and FIG. 28(a) represent the side having the radiation plane of the illumination apparatus, and FIG. 27(b) and FIG. 28(b) represent the back side of the illumination apparatus.

As shown in FIG. 27, the configuration having more lenses 200 (and light emitting devices 330) than illumination apparatus 1 shown in FIG. 2 may be employed. In the example shown in FIG. 27, the diameter of a center hole 700A is basically larger than the diameter of center hole 700 of illumination apparatus 1 shown in FIG. 2. It is noted that the same lens 200 as lens 200 used in illumination apparatus 1 shown in FIG. 2 can be used.

On the other hand, as shown in FIG. 28, the configuration having fewer lenses 200 (and light emitting devices 330) than illumination apparatus 1 shown in FIG. 2 may be employed. In the example shown in FIG. 28, the diameter of a center hole 700B is basically larger than the diameter of center hole 700 of illumination apparatus 1 shown in FIG. 2. It is noted that the same lens 200 as lens 200 used in illumination apparatus 1 shown in FIG. 2 can be used.

<<K. Controller for Turning On>>

Figure 29:
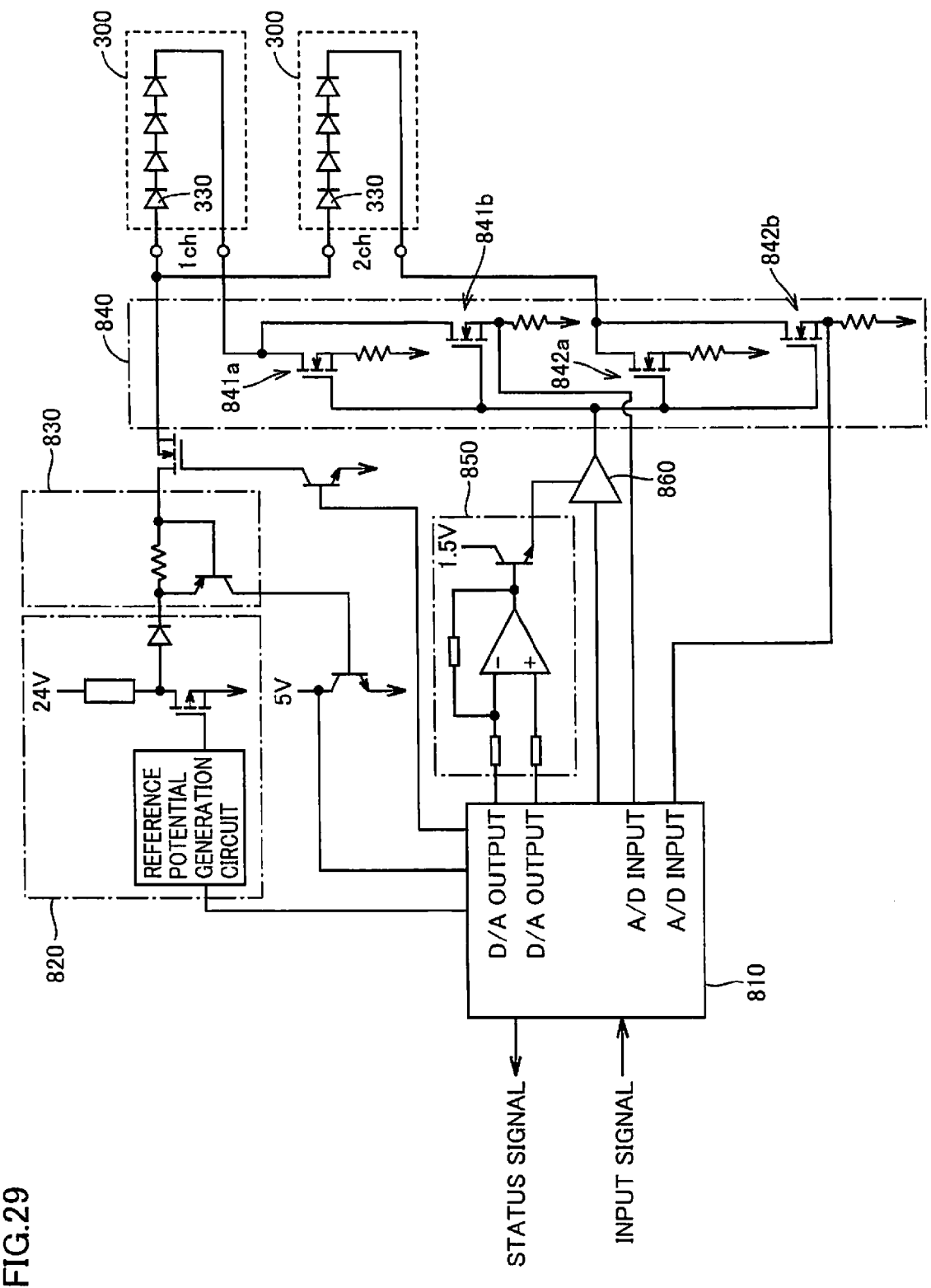
FIG. 29 is a schematic diagram showing a circuit configuration of a controller for turning on according to the embodiment of the present invention.
Figure 30:
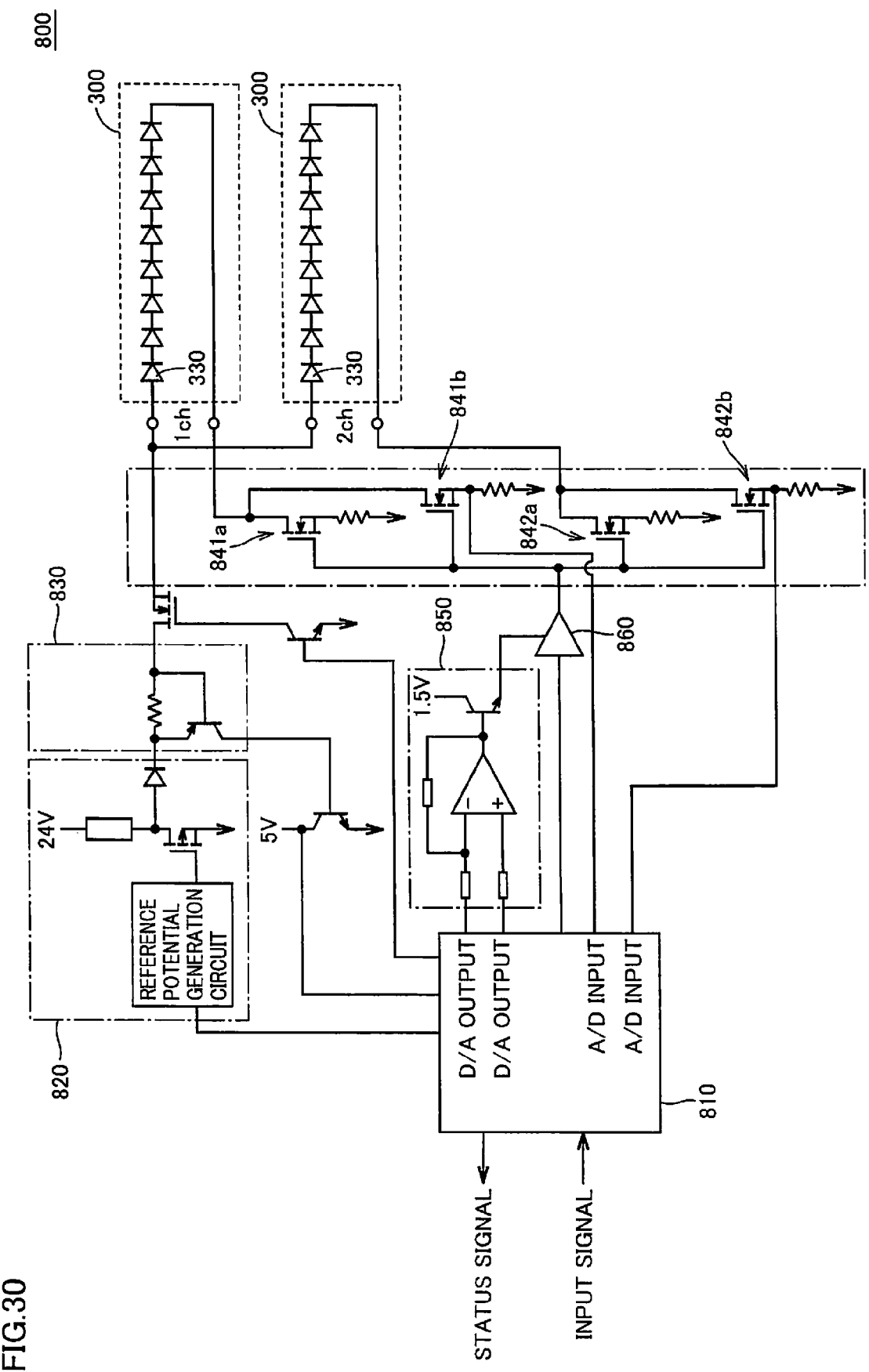
FIG. 30 is a schematic diagram showing a circuit configuration of a controller for turning on according to the embodiment of the present invention.
Figure 31:
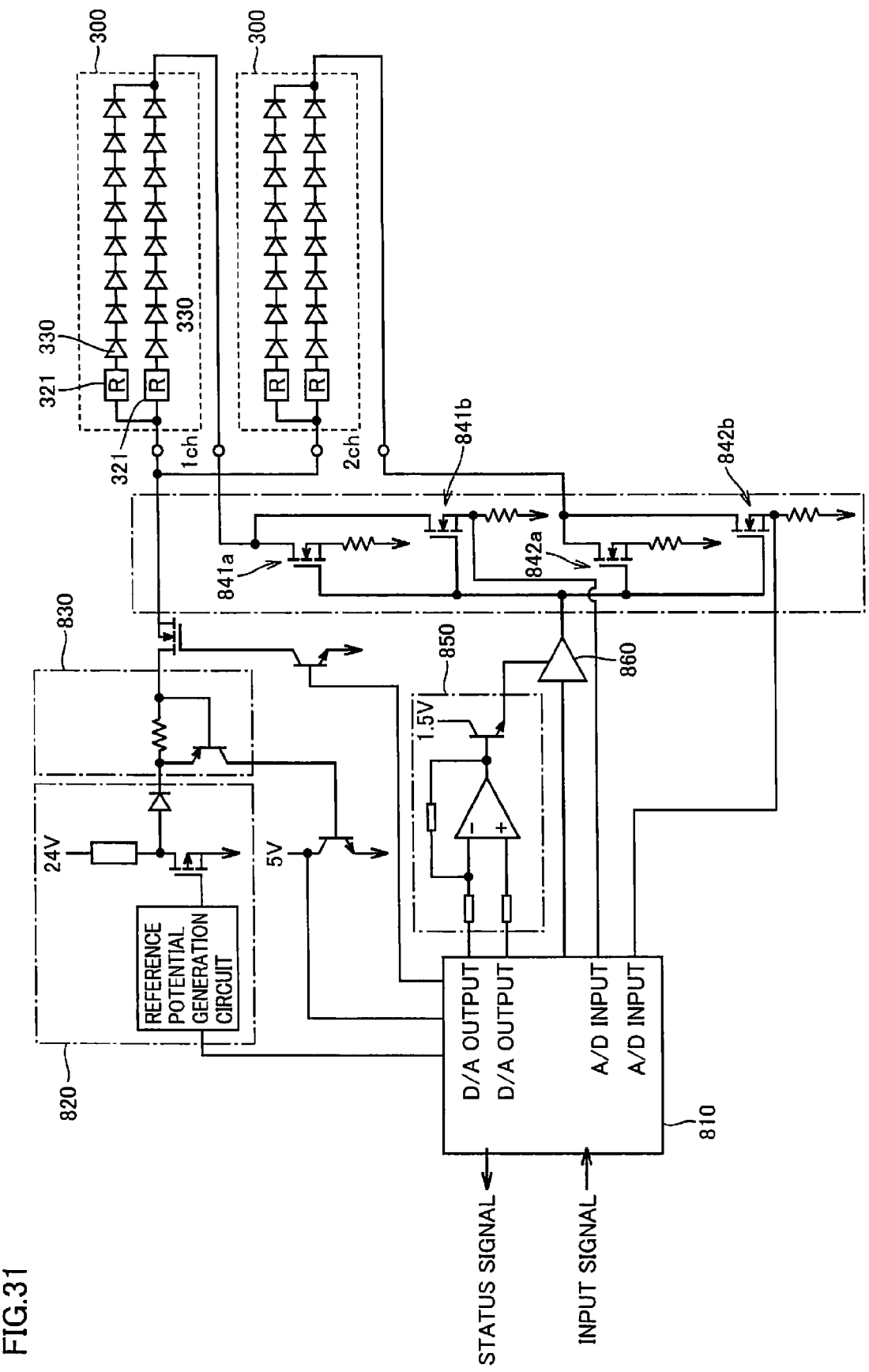
FIG. 31 is a schematic diagram showing a circuit configuration of a controller for turning on according to the embodiment of the present invention.

A controller (power supply portion) for turning on illumination apparatus I described above will now be described. FIG. 29 to FIG. 31 are diagrams each showing a circuit configuration of a controller 800 for turning on according to the embodiment of the present invention.

Referring to FIG. 29, controller 800 includes a control circuit 810, a step-up circuit 820, an overcurrent detection circuit 830, a constant current circuit 840, and a constant voltage circuit 850. Control circuit 810 provides a control signal to each circuit according to an externally input signal to supply requested current to illumination apparatus 1 (light emitting device 330). Control circuit 810 outputs a status signal to the outside to indicate the present state of current supply and the like.

Step-up circuit 820 converts an input voltage (24 V) into a voltage designated beforehand and outputs the converted voltage. Step-up circuit 820 has a transistor (typically, FET (Field Effective Transistor) disposed in series between an input and a ground node for receiving a command value corresponding to a voltage to be output from a reference potential generation circuit.

Overcurrent detection circuit 830 is a circuit for limiting current flowing through the connected light emitting device 330 to prevent current from becoming excessive. Specifically, overcurrent detection circuit 830 has a resistor element inserted on a current supply path, and the supply current flows through the resistor element to produce a potential difference, which is applied between the base and the emitter of a transistor. When a voltage exceeding a predetermined threshold value is generated between both ends of the resistor element, the transistor is rendered conductive. This status change of the transistor is provided to control circuit 810. Control circuit 810 stops or temporarily cuts off power supply by controller 800 in response to the signal from overcurrent detection circuit 830.

Constant current circuit 840 supplies current at a predetermined constant value to the connected light emitting device 330. Constant current circuit 840 shown in FIG. 29 provides power supply in two routes (1 ch and 2 ch). In constant current circuit 840, transistors (typically, FET) for controlling current are connected in parallel so that current can be supplied to more light emitting devices 330 in each route. Specifically, constant current drivers 841a and 841b are connected in parallel to 1 ch, and constant current drivers 842a and 842b are connected in parallel to 2 ch.

Constant current circuit 840 feeds a current value according to a command from a FET driver 860. Power for driving FET driver 860 is supplied from constant voltage circuit 850. Constant voltage circuit 850 decreases a control voltage (1.5 V) to a designated voltage according to a command signal from control circuit 810 and outputs the decreased voltage to FET driver 860.

As described above, controller 800 in the present embodiment can output current for driving light emitting device 330 in two routes. Therefore, as shown in FIG. 29, rigid flexible substrates 300 each having four light emitting devices 330 connected in series can be driven independently from each other. Though depending on a forward voltage of light emitting device 330, as many light emitting devices 330 as desired can be connected in series as long as the total value of the forward voltages does not exceed the voltage value that can be output from controller 800.

For example, FIG. 30 shows an example in which two rigid flexible substrates 300 each having eight series-connected light emitting devices 330 are driven. When more light emitting devices 330 are driven at the same time, as shown in FIG. 31, as many strings of series-connected light emitting devices 330 as desired may be mounted on one rigid flexible substrate 300, within the upper limit value. In this case, a limiting resistor 321 is preferably inserted in each string in order to suppress an imbalance of current flowing through each string.

As described above, the brightness generated by each light emitting device 330 can be controlled appropriately by controlling the magnitude of current flowing through a plurality of light emitting devices 330 connected in series. As a result, when the ring-shaped illumination apparatus 1 is configured, partial unevenness in brightness can be prevented.

<<L. Advantages>>

According to the present embodiment, holding portion 110 provided in base 100 can be used to position and fix lens 200 and unit substrate 320 having the corresponding light emitting device 330 mounted thereon. In this manner, optical components necessary for light radiation can be attached with reference to the casing, thereby increasing reliability and maintaining the optical accuracy.

According to the present embodiment, holding portion 110 provided in base 100 can be used to generally fix lens 200 and unit substrate 320, thereby simplifying the structure for fixing these optical components from the back side. Accordingly, the number of components can be reduced thereby reducing the cost. In addition, the number of assembly steps can be reduced. Furthermore, the reduction in number of assembly steps can increase the reliability.

According to the present embodiment, holding portion 110 provided in base 100 can restrain lens 200 from moving toward the radiation plane, thereby eliminating the possibility that lens 200 drops toward the work. The reliability can be increased also in this sense.

According to the present embodiment, light emitting device 330 is mounted on unit substrate 320 formed as a body (rigid body) made of a relatively hard material, while flexible substrate 340 made of a relatively soft material connected to unit substrate 320 is formed in a concentric shape, whereby light emitting device 330 is positioned. Therefore, mechanical stress on light emitting device 330 can be prevented.

The embodiment disclosed here should be understood as being illustrative rather than being limitative in all respects. The scope of the present invention is shown not in the foregoing description but in the claims, and it is intended that all modifications that come within the meaning and range of equivalence to the claims are embraced here.

Reference Signs List

1, 1A, 1B illumination apparatus, 2 camera, 3 image processing apparatus, 4 production line, 100 base, 102 window, 110 holding portion, 111 snap fit, 112, 116 end restraining portion, 114, 115, 118 side restraining portion, 117 light press-fitting pawl, 130 fitting hole, 140, 540 screw hole, 150, 550 power supply cable-through concave portion, 160 radiation plane, 170 opening, 180 clearance, 200, 200A lens, 202, 203 convex portion, 204, 205, 208, 209, 212, 213 contact surface, 210 concave portion, 214 reflection plane, 300, 300A, 300B, 300C, 300D, 300E, 300F rigid flexible substrate, 320, 320A, 320B, 320C, 320D, 320E unit substrate, 321 limiting resistor, 322a, 322b land, 324 hole, 326 gap, 330 light emitting device, 340, 340A, 340B, 340D, 340E flexible substrate, 351, 352, 353, 354 connector, 400 heat sink sheet, 402 cut, 500 case, 512 pressing portion, 520 accommodation space, 530 fitting pawl, 600 power supply cable, 601 wire, 700, 700A, 700B center hole, 800 controller, 810 control circuit, 820 step-up circuit, 830 overcurrent detection circuit, 840 constant current circuit, 841 a, 842a constant current driver, 850 constant voltage circuit, 860 FET driver, SYS vision sensor system, W work.

The invention claimed is:

1. An illumination apparatus comprising:
   a plurality of lenses;
   a first casing that has a radiation plane provided with a plurality of annularly arranged windows for attaching said plurality of lenses, respectively, independently, and that has an opening at a position opposite to said radiation plane;
   a first substrate associated with each of said plurality of lenses and accordingly disposed, said first substrate each having at least one light emitting device mounted thereon; and
   a second casing closing said opening of said first casing, wherein:
   said first casing includes a holding portion associated with each of said plurality of windows; and
   said holding portion each permits said lens to be attached to said first casing from a side thereof having said opening and also restrains said lens from moving through said first casing toward said radiation plane, and when said lens is attached to said first casing said lens has an optical axis in a direction having a predetermined angle relative to a center axis of said first casing.

2. The illumination apparatus according to claim 1, further comprising a second substrate for electrical connection between said first substrate and another said first substrate, wherein:

said first substrate is configured as a rigid body; and
said second substrate is configured to have flexibility.

3. The illumination apparatus according to claim 2, wherein:
said second substrate is bent in accordance with how said plurality of windows are arranged; and
said first substrate is each bent relative to an associated portion of said second substrate at an angle corresponding to an inclination of said lens held by said holding portion.

4. The illumination apparatus according to claim 3, wherein said holding portion each further holds said first substrate to maintain a predetermined, relative, positional relationship with said lens.

5. The illumination apparatus according to claim 2, wherein said second casing includes a pressing portion for pressing each said first substrate that has been attached to said first casing toward said radiation plane when said second casing is coupled with said first casing.

6. The illumination apparatus according to claim 5, wherein said pressing portion is each configured to press opposite ends of said first substrate associated therewith.

7. The illumination apparatus according to claim 5, further comprising a heat conducting and elastic sheet inserted between said first substrate and said pressing portion of said second casing.

8. The illumination apparatus according to claim 7, wherein said sheet is generally round, and also has a cut and is thus sectioned to correspond to how said first substrate is arranged.

9. The illumination apparatus according to claim 2, further comprising a power supply cable penetrating said first and second casings and thus introduced therein, wherein:
said second substrate includes a pair of connectors for electrical connection to said power supply cable; and
said pair of connectors are provided in a direction corresponding to a position at which said power supply cable is introduced.

* * * * *